(12) United States Patent
Kontham et al.

(10) Patent No.: US 11,339,174 B2
(45) Date of Patent: May 24, 2022

(54) γ-SPIROKETAL-γ-LACTONES AND PHARMACEUTICAL COMPOSITION CONTAINING SAME AND PROCESS FOR PREPARATION THEREOF

(71) Applicant: Council of Scientific and Industrial Research, New Delhi (IN)

(72) Inventors: Ravindar Kontham, Pune (IN); Digambar Abasaheb Kambale, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 134 days.

(21) Appl. No.: 16/610,383

(22) PCT Filed: Apr. 27, 2018

(86) PCT No.: PCT/IN2018/050263
§ 371 (c)(1),
(2) Date: Nov. 1, 2019

(87) PCT Pub. No.: WO2018/203346
PCT Pub. Date: Nov. 8, 2018

(65) Prior Publication Data
US 2021/0198273 A1   Jul. 1, 2021

(30) Foreign Application Priority Data

May 2, 2017 (IN) .............................. 201711015471

(51) Int. Cl.
*C07D 493/10*   (2006.01)
(52) U.S. Cl.
CPC .................................. *C07D 493/10* (2013.01)
(58) Field of Classification Search
CPC .................................................. C07D 493/10
See application file for complete search history.

(56) References Cited

FOREIGN PATENT DOCUMENTS

CN         101565444 A      10/2009

OTHER PUBLICATIONS

Cancer and Metastasis Reviews (1998), 17(1), 91-106.*
Science (1999), vol. 286, 531-537.*
Registry No. 924294-81-5, File Registry on STN, 2 entered STN Mar. 2, 2007.*
Yang et al., Eur. J. Org. Chem. 2006, 5394-5403.*
Avonto et al. Toxicology and Applied Pharmacology 318 (2017) 16-22.*
International Search Report and Written Opinion for PCT/IN2018/050263, dated Jul. 17, 2018, 4 pages.
Tang et al., "Lewis acid-mediated reactions of 1-cyclopropyl-2-arylethanone derivatives with diethyl 2-oxomalonate and ethyl 2-oxoacetate" Tetrahedron 65 (2009) pp. 9336-9343.
Yang, et al. "A Stereoselective Synthetic Route to 1,6-Dioxaspiri[4,4]non-3-en-2-ones from Cyclopropyl Alkyl Ketones and α-Ketoesters." Chem., Shanghai Inst. Org. Chem., Chin. Acad. Sci., Shanghai 200032, 2006, vol. 8, No. 8,1709-1712.
Quach, "Recent developments in transition metal-catalysed spiroketalisation", Org. Biomol. Chem., 2014, 12, pp. 7423-7432.
Kovacevic et al. "Synthesis and in vitro antitumour activity of crassalactone D, its stereoisomers and novel cinnamic ester derivatives" European Journal of Medicinal Chemistry 134 (2017) pp. 293-303.
Kovacević et al. "Synthesis and antiproliferative activity of goniobutenolides A and B, 5-halogenated crassalactone D derivatives and the corresponding 7-epimers" European Journal of Medicinal Chemistry 108 (2016) pp. 594-604.
Mo, et al. "Two New Cycloartane Triterpenoids from *Kleinhovia hospital*", Helvetica Chimica Acta—vol. 97 (2014) pp. 887-894.
Yang et al. "Asymmetric Total Synthesis of (+)-Crassalactone D", J. Org. Chem. 2009, 74, pp. 9546-9549.

* cited by examiner

*Primary Examiner* — Rebecca L Anderson
(74) *Attorney, Agent, or Firm* — Blank Rome LLP

(57) ABSTRACT

The present invention relates to γ-spiroketal-γ-lactones of formula (I) or a stereoisomer, ester, hydrate, solvate or pharmaceutically acceptable salt thereof and a pharmaceutically acceptable carrier, diluent or excipient and a process for preparation thereof. The present invention further provides a pharmaceutical composition comprising γ-spiroketal-γ-lactones of formula (I) or a salt thereof.

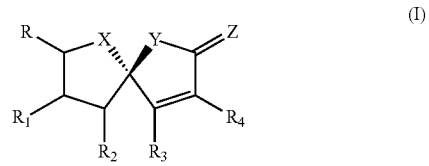

4 Claims, No Drawings

γ-SPIROKETAL-γ-LACTONES AND PHARMACEUTICAL COMPOSITION CONTAINING SAME AND PROCESS FOR PREPARATION THEREOF

RELATED APPLICATIONS

This application is a national phase of PCT/IN2018/050263, filed on Apr. 27, 2018, which claims the benefit of Indian Application No. 201711015471, files on May 2, 2017.

TECHNICAL FIELD OF THE INVENTION

The present invention relates to Γ-spiroketal-γ-lactones of formula (I) or a stereoisomer, ester, hydrate, solvate or pharmaceutically acceptable salt thereof and a pharmaceutically acceptable carrier, diluent or excipient and a process for preparation thereof.

BACKGROUND AND PRIOR ART OF THE INVENTION

Spiroketals and oxa-spirolactones are ubiquitous chemical entities found in a myriad of pharmacologically important natural products. In recent times, it has been shown that simplified spiroacetals derived from natural products retain their biological properties. Hence, these scaffolds essentially contribute to biological activities and represent privileged pharmacophores in drug discovery. In the recent years, several bioactive natural products with unsaturated γ-spiroketal-γ-lactone (1,6-dioxaspiro[4.4]non-3-en-2-one) appendage were isolated and have become an important sub-group of spiroketals, which include pyrenolide D (anti-cancer, IC50=4 µg/mL against HL-60), crassalactone D (anticancer, ED50=1.1 µg/mL against P-388, 3.3 µg/mL against KB, 4.0 µg/mL against Col-2, 3.2 µg/mL against BCA-1 and 3.1 µg/mL against ASK), massarinoline A (active against *Bacillus subtilis* and *Staphylococcus aureus*), levantenolide (antibacterial & anticancer), tuberostemonamide (antitussive), papyracillic acid C (anti-biotic), acutissimatriterpene A (herbal medicine), 10 aphagrandinoid A (antibacterial) and many others.

Article titled "Lewis acid-mediated reactions of 1-cyclopropyl-2-arylethanone derivatives with diethyl 2-oxomalonate and ethyl 2-oxoacetate" by Xiang-Ying Tang et al. published in Tetrahedron, 2009, 65, pp 9336-9343 reports TMSOTf-mediated reactions of 2-aryl-1-(1-phenylcyclopropyl)ethanones 1 with diethyl 2-oxomalonate 2 afford a novel method for the synthesis of spiro-γ-lactone derivatives 3 in good to excellent yields via a sequential reaction involving a nucleophilic ring-opening reaction of the cyclopropane by H₂O, an aldol-type reaction and a cyclic transesterification mediated by Lewis acid. On the other hand, TMSOTf-mediated reactions of 1-cyclopropyl-2-arylethanones 1 with ethyl 2-oxoacetate 4 could also provide the corresponding spiro-γ-lactone derivatives 5 in moderate yields along with another spiro-γ-lactone derivatives 6 derived from the reaction of 1 with two molecules of ethyl 2-oxoacetate.

Article titled "A Stereoselective Synthetic Route to 1,6-Dioxaspiro[4.4]non-3-en-2-ones from Cyclopropyl Alkyl Ketones and α-Ketoesters" by Yong-Hua Yang et al. published in Organic Letters, 2006, Vol. 8, No. 8,1709-1712 reports the SnCl4-mediated reactions of cyclopropyl alkyl ketones with γ-ketoesters afford a novel method for the synthesis of 1,6-dioxaspiro[4.4]-non-3-en-2-ones with high stereo selectivities in moderate to good yields. This process is a sequential reaction involving a nucleophilic ring opening reaction of the cyclopropane by H₂O, an aldol-type reaction, and a cyclic transesterification mediated by Lewis acid.

Article titled "Recent developments in transition metal-catalysed spiroketalisation" by Rachelle Quach et al. published in Organic & Biomolecular Chemistry, 2014, 12, 7423 reports investigation of $Pd^{II}$, $Pt^{II}$, $Au^{I}$, $Au^{III}$, and $Re^{VII}$ have all been investigated for their ability to construct the spiroketal moiety. Recent developments have explored numerous novel cyclisations and their application to the synthesis of spiroketal-containing natural products. Developments include new catalytic protocols, exploration of chiral ligands and the novel application of known reactions to the synthesis of spiroketals. This Perspective covers recent metal-catalysed syntheses of spiroketals (published since 2012) in this rapidly-developing field.

All of these approaches had several limitations such as usage of prefunctionalized starting materials, protection and deprotection sequence, stoichiometric amount of Lewis acids and multiple steps.

Therefore, there is a need for the development of new synthetic approaches for unsaturated γ-spiroketal-γ-lactones is of considerable importance in the fields of both synthetic and medicinal chemistry.

OBJECTS OF THE PRESENT INVENTION

Main objective of the present invention is to provide γ-spiroketal-γ-lactones of formula (I) or a stereoisomer, ester, hydrate, solvate or pharmaceutically acceptable salt thereof and a pharmaceutically acceptable carrier, diluent or excipient.

Another objective of the present invention is to provide pharmaceutical composition containing γ-spiroketal-γ-lactones of formula (I) or a stereoisomer, ester, hydrate, solvate or pharmaceutically acceptable salt thereof and a pharmaceutically acceptable carrier, diluent or excipient.

Yet another objective of the present invention is to provide a process for the preparation of γ-spiroketal-γ-lactones of formula (I) or a stereoisomer, ester, hydrate, solvate or pharmaceutically acceptable salt thereof and a pharmaceutically acceptable carrier, diluent or excipient.

SUMMARY OF THE PRESENT INVENTION

Accordingly, the present invention provides γ-spiroketal-γ-lactones of formula (I) or a stereoisomer, ester, hydrate, solvate or pharmaceutically acceptable salt thereof and a pharmaceutically acceptable carrier, diluent or excipient,

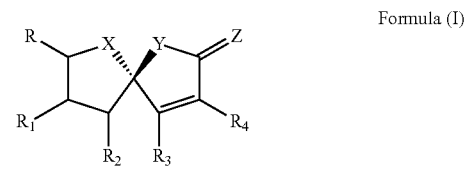

Formula (I)

wherein R, $R_1$, $R_2$, $R_3$ and $R_4$ represents independently of each other hydrogen, alkyl, cycloalkyl, alkene, alkyne, alkenyl, aryl, heteroaryl, monocyclic or bicyclic heteroarylene group having at least one heteroatom selected from the group consisting of N, S and O, halogen, hydroxy, cyano, amino, alkoxy; and X, Y and Z each is O.

The present invention further provides one step process for the preparation of γ-spiroketal-γ-lactones of formula (I) or a stereoisomer, ester, hydrate, solvate or pharmaceutically acceptable salt thereof and a pharmaceutically acceptable carrier, diluent or excipient comprising adding catalyst in the solution of alkynol and γ-ketoester in suitable solvent at a temperature ranging from 25° C. to 30° C. followed by stirring the reaction mixture at the temperature ranging from 25° C. to 30° C. for a time period 12 to 48 hours to obtain γ-spiroketal-γ-lactone of formula (I).

DETAILED DESCRIPTION OF THE PRESENT INVENTION

The present invention will now be described in detail in connection with certain preferred and optional embodiments, so that various aspects thereof may be fully understood and appreciated.

In an embodiment, the present invention provides γ-spiroketal-γ-lactones of formula (I) or a stereoisomer, ester, hydrate, solvate or pharmaceutically acceptable salt thereof and a pharmaceutically acceptable carrier, diluent or excipient,

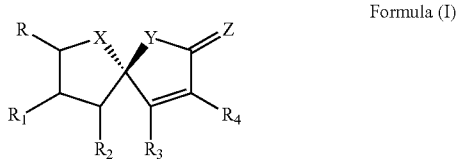

Formula (I)

wherein R, $R_1$, $R_2$, $R_3$ and $R_4$ represents independently of each other hydrogen, alkyl, cycloalkyl, alkene, alkyne, alkenyl, aryl, heteroaryl, monocyclic or bicyclic heteroarylene group having at least one heteroatom selected from the group consisting of N, S and O, halogen, hydroxy, cyano, amino, alkoxy; and X, Y and Z each independently is O.

In a preferred embodiment, said γ-spiroketal-γ-lactones of formula (I) is selected from the group consisting of 3-Methyl-1, 14-dioxadispiro [4.1.5$^7$.2$^5$] tetradec-3-en-2-one (1), 3-Phenyl-1, 14-dioxadispiro [4.4.5$^7$.2$^5$] tetradec-3-en-one (2), 3-(4-Methoxyphenyl)-1, 14-dioxadispiro [4.1.5$^7$.2$^5$] tetradec-3-en-2-one (3), 3-(p-Tolyl)-1, 14-dioxadispiro [4.1.5$^7$.2$^5$] tetradec-3-en-2-one (4), 3-Methyl-1, 13-dioxadispiro [4.1.4$^7$.2$^5$] tridec-3-en-2-one (5), 3-Phenyl-1, 13-dioxadispiro [4.1.4$^7$.2$^5$] tridec-3-en-one (6), 3-(4-Methoxyphenyl)-1, 13-dioxadispiro [4.1.4$^7$.2$^5$] tridec-3-en-2-one (7), 3-(p-Tolyl)-1, 13-dioxadispiro [4.1.4$^7$.2$^5$] tridec-3-en-2-one (8), 3-(4-Nitrophenyl)-1, 13-dioxadispiro [4.1.4$^7$.2$^5$] tridec-3-en-2 (9), 3-Methyl-1, 6-dioxaspiro [4.4] non-3-en-2-one (10), 3-Phenyl-1, 6-dioxaspiro [4, 4] non-3-en-2-one (11), 3-(4-Methoxyphenyl)-1, 6-dioxaspiro [4, 4] non-3-en-2-one (12), 3-(p-Tolyl)-1,6-dioxaspiro[4.4]non-3-en-2-one (13), 3, 4-Dimethyl-1, 14-dioxadispiro [4.1.5$^7$.2$^5$] tetradec-3-en-2-one (14), 4-Methyl-3-phenyl-1, 14-dioxadispiro [4.1.5$^7$.2$^5$] tetradec-3-en-2-one (15), 3-(4-Methoxyphenyl)-4-methyl-1, 14-dioxadispiro [4.1.5$^7$.2$^5$] tetradec-3-en-2-one (16), 4-Methyl-3-(p-tolyl)-1, 14-dioxadispiro [4.1.5$^7$.2$^5$] tetradec-3-en-2-one (17), 4-Ethyl-3-methyl-1, 14-dioxadispiro [4.1.5$^7$.2$^5$] tetradec-3-en-2-one (18), 4-Ethyl-3-phenyl-1, 14-dioxadispiro [4.1.5$^7$.2$^5$] tetradec-3-en-2-one (19), 4-Ethyl-3-(4-methoxyphenyl)-1, 14-dioxadispiro [4.1.5$^7$.2$^5$] tetradec-3-en-2-one (20), 4-Ethyl-3-(p-tolyl)-1, 14-dioxadispiro [4.1.5$^7$.2$^5$] tetradec-3-en-2-one (21), 3-Methyl-4-phenyl-1, 14-dioxadispiro [4.1.5$^7$.2$^5$] tetradec-3-en-2-one (22), 3, 4-Diphenyl-1, 14-dioxadispiro [4.1.5$^7$.2$^5$] tetradec-3-en-2-one (23), 3-(4-Methoxyphenyl)-4-phenyl-1, 14-dioxadispiro [4.1.5$^7$.2$^5$] tetradec-3-en-2-one (24), 4-Phenyl-3-(p-tolyl)-1, 14-dioxadispiro [4.1.5$^7$.2$^5$] tetradec-3-en-2-one (25), 3-(4-Nitrophenyl)-4-phenyl-1, 14-dioxadispiro [4.1.5$^7$.2$^5$] tetradec-3-en-2-one (26), 3-Methyl-4-phenyl-1, 13-dioxadispiro [4.1.4$^7$.2$^5$] tridec-3-en-2-one (27), 3-(4-Nitrophenyl)-4-phenyl-1, 13-dioxadispiro [4.1.4$^7$.2$^5$] tridec-3-en-2-one (28), 3-Methyl-4-phenyl-1,6-dioxaspiro[4.4]non-3-en-2-one (29), 3,4-Diphenyl-1,6-dioxaspiro[4.4]non-3-en-2-one (30), 3-(4-Nitrophenyl)-4-phenyl-1, 6-dioxaspiro [4.4] non-3-en-2-one (31), 3-methyl-8, 8-diphenyl-1, 6-dioxaspiro [4.4] non-3-en-2-one (32), 3, 8, 8-triphenyl-1, 6-dioxaspiro [4.4] non-3-en-2-one (33), 3-methyl-7-phenyl-1,6-dioxaspiro[4.4]non-3-en-2-one (34), 4'-methyl-3a,4,5,6,7,7a-hexahydro-3H,5'H-spiro[benzofuran-2,2'-furan]-5'-one (35), 4-methyl-3a'-(prop-2-yn-1-yl)-3',3a',4',8b'-tetrahydro-5H-spiro[furan-2, 2'-indeno[1,2-b]furan]-5-one (36), 4-phenyl-3a'-(prop-2-yn-1-yl)-3',3a',4', 8b'-tetrahydro-5H-spiro[furan-2,2'-indeno[1, 2-b]furan]-5-one (37), 4-methyl-3a'-(prop-2-yn-1-yl)-3a', 4',5 ',9b'-tetrahydro-3 'H, 5H-spiro [furan-2,2'-naphtho [1,2-b]furan]-5-one (38), 4-phenyl-3a'-(prop-2-yn-1-yl)-3a',4',5 ',9b'-tetrahydro-3 'H,5H-spiro [furan-2,2'-naphtho[1,2-b]furan]-5-one (39), (E)-3-styryl-1, 13-dioxadispiro[4.1.4$^7$.2$^5$] tridec-3-en-2-one (40), 3-methyl-4, 8, 8-triphenyl-1, 6-dioxaspiro [4.4] non-3-en-2-one (41), 4'-methyl-3'-phenyl-3a, 4, 5, 6, 7, 7a-hexahydro-3H, 5'H-spiro [benzofuran-2, 2'-furan]-5'-one (42).

In another preferred embodiment, the γ-spiroketal-γ-lactones of formula (I) is used as anticancer and antibacterial, antimalarial, antifungal agent.

In another embodiment, the present invention provides one step process for the preparation of γ-spiroketal-γ-lactones of formula (I) or a stereoisomer, ester, hydrate, solvate or pharmaceutically acceptable salt thereof and a pharmaceutically acceptable carrier, diluent or excipient comprising adding catalyst in the solution of alkynol and γ-ketoester in suitable solvent at a temperature ranging from 25° C. to 30° C. followed by stirring the reaction mixture at the temperature ranging from 25° C. to 30° C. for a time period 12 to 48 hours to afford γ-spiroketal-γ-lactone of formula (I).

The alkynol is selected from (1-(Prop-2-yn-1-yl) cyclohexyl) methanol, (1-(But-2-yn-1-yl) cyclohexyl) methanol, (1-(Pent-2-yn-1-yl) cyclohexyl) methanol, (1-(3-Phenylprop-2-yn-1-yl) cyclohexyl), (1-(Prop-2-yn-1-yl) cyclopentyl) methanol, (1-(3-Phenylprop-2-yn-1-yl) cyclopentyl) methanol, 5-Phenylpent-4-yn-1-ol, 2, 2-diphenylpent-4-yn-1-ol, 1-phenylpent-4-yn-1-ol, 2-(prop-2-yn-1-yl)cyclohexan-1-ol, 2,2-di(prop-2-yn-1-yl)-2,3-dihydro-1H-inden-1-ol, 2,2-di(prop-2-yn-1-yl)-1,2,3,4-tetrahydronaphthalen-1-ol, 2,2,5-triphenylpent-4-yn-1-ol, 2-(3-phenylprop-2-yn-1-yl) cyclohexan-1-ol.

The ketoester is selected from ethyl 2-(4-nitrophenyl)-2-oxoacetate, ethyl pyruvate, ethyl phenylglyoxylate, ethyl anisylglyoxylate, ethyl p-tolylglyoxylate, ethyl (E)-2-oxo-4-phenylbut-3-enoate.

The catalyst is selected from bismuth triflate Bi(OTf)$_3$, Copper (II) triflate (Cu(OTf)$_2$), Scandium(III) triflate (Sc(OTf)$_3$), Ferric triflate (Fe(OTf)$_2$), mercuric triflate (Hg(OTf)$_2$), Ytterbium triflate (Yb(OTf)$_3$), Iron(III) chloride (FeCl$_3$), Silver triflate (AgOTf), p-Toluenesulfonic acid (PTSA), Trifluoromethanesulfonic acid (TfOH).

The solvent is selected from dicholoromethane (CH$_2$Cl$_2$), toluene, acetonitrile (CH$_3$CN), Tetrahydrofuran (THF), Nitromethane (CH$_3$NO$_2$).

The yield of the process of the present invention is 40-80%.

The above process as shown in following scheme:

Scheme 1

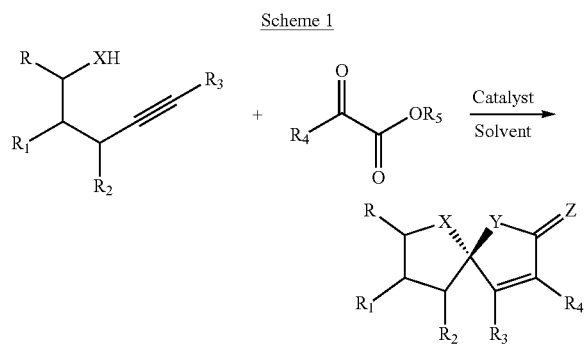

Wherein R, $R_1$, $R_2$, $R_3$, $R_4$ and $R_5$ each independently are hydrogen, alkyl, cycloalkyl, alkene, alkyne, alkenyl, aryl, heteroaryl, monocyclic or bicyclic heteroarylene group having at least one heteroatom selected from the group consisting of N, S and O, halogen, hydroxy, cyano, amino, alkoxy; and X, Y and Z each independently is O.

In still another embodiment, the present invention provides a process of preparation of 3-Methyl-1, 14-dioxadispiro [4.1.57.25] tetradec-3-en-2-one

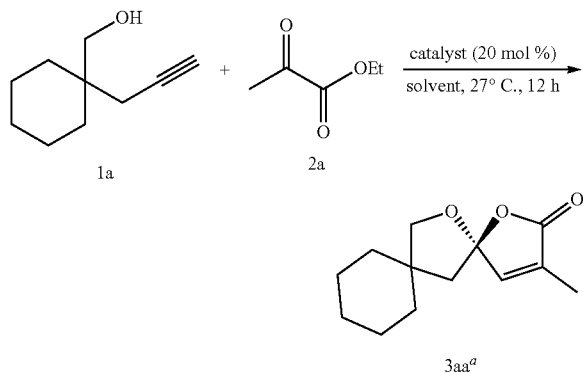

TABLE 1

Optimization of the reaction conditions

| Entry | Catalyst | Solvent | Yield (%) |
|---|---|---|---|
| 1 | Bi(OTf)$_3$ | CH$_2$Cl$_2$ | 80 |
| 2 | Bi(OTf)$_3$ | toluene | 70 |
| 3 | Bi(OTf)$_3$ | CH$_3$CN | 64 |
| 4 | Bi(OTf)$_3$ | THF | 65 |
| 5 | Cu(OTf)$_2$ | CH$_2$Cl$_2$ | 60 |
| 6 | Sc(OTf)$_3$ | CH$_2$Cl$_2$ | — |
| 7 | Fe(OTf)$_2$ | CH$_2$Cl$_2$ | 40 |
| 8 | In(OTf)$_3$ | CH$_2$Cl$_2$ | 68 |
| 9 | Hg(OTf)$_2$ | CH$_2$Cl$_2$ | 70 |
| 10 | Hg(OTf)$_2$ | CH$_3$CN | 50 |
| 11 | Yb(OTf)$_3$ | CH$_2$Cl$_2$ | — |
| 12 | FeCl$_3$ | CH3CN | 50 |
| 13 | FeCl$_3$ | CH$_2$Cl$_2$ | — |
| 14 | AgOTf | CH$_2$Cl$_2$ | 70 |
| 15 | AgOTf | THF | 60 |
| 16 | PTSA | CH$_3$NO$_2$ | — |

TABLE 1-continued

Optimization of the reaction conditions

| Entry | Catalyst | Solvent | Yield (%) |
|---|---|---|---|
| 17 | PTSA | THF | 62 |
| 18 | TfOH | CH$_2$Cl$_2$ | — |
| 19 | No Catalyst | CH$_2$Cl$_2$ | — |
| 20 | Bi(OTf)$_3$, MS-4 Å | CH$_2$Cl$_2$ | — |

In yet another embodiment, the present invention provides pharmaceutical composition comprising a compound of formula (I) or a stereoisomer, ester, isomer, hydrate, solvate or pharmaceutically acceptable salt thereof and a pharmaceutically acceptable carrier, diluent or excipient.

In still yet another embodiment, the present invention provides a method for treating fungus, bacterial, malarial infection, or cancer in a subject in need thereof; comprising administering to the subject a therapeutically effective amount of the γ-spiroketal-γ-lactones of formula (I) or a stereoisomer, ester, isomer, hydrate, solvate or pharmaceutically acceptable salt thereof and a pharmaceutically acceptable carrier, diluent or excipient.

The compounds of the present invention possess antibacterial activity against a wide spectrum of Gram-positive and Gram-negative bacteria, aerobic and anaerobic organisms such as *Staphylococcus, Lactobacillus, Streptococcus, Escherichia, Enterobacter, Pseudomonas, Proteus, Citrobacter, Baccillus, Clostridium, Salmonella*, and other organisms. Also, the compounds of the present invention possess antibacterial activity against bacterial species resistant to conventional [beta]-lactams, such as MRSA. Further, the compounds of the instant invention are effective as antiplasmodium agent for the treatment of malaria. The compound of formula (I) disclosed herein is present in the composition in an amount which is effective to treat the disease or the condition caused by the bacterial strains mentioned above. The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, injections, gels and microspheres, In another embodiment, the present invention relates to administering 'an effective amount' of the 'composition of invention' to the subject suffering from said disease. Accordingly, compound of formula I and pharmaceutical compositions containing them may be administered using any amount, any form of pharmaceutical composition via any route of administration effective for treating the disease. Typical routes of administering such pharmaceutical compositions include, without limitation, oral, topical, transdermal, inhalation, parenteral, sublingual, buccal, rectal, vaginal, and intranasal.

Pharmaceutical compositions of the invention are formulated so as to allow the active ingredients contained therein to be bioavailable upon administration of the composition to a patient. Compositions that will be administered to a subject or patient may take the form of one or more dosage units. The dosage forms can also be prepared as sustained, controlled, modified and immediate dosage forms.

The following examples, which include preferred embodiments, will serve to illustrate the practice of this invention, it being understood that the particulars shown are by way of examples and for purpose of illustrative discussion of preferred embodiments of the invention only and are not limiting the scope of the invention.

The term "pharmaceutically acceptable" means that which is useful in preparing a pharmaceutical composition that is generally non-toxic and is not biologically undesirable and includes that which is acceptable for veterinary use and/or human pharmaceutical use. The term "pharmaceutical composition" is intended to encompass a drug product including the active ingredient(s), pharmaceutically acceptable excipients that make up the carrier, as well as any product which results, directly or indirectly, from combination, complexation or aggregation of any two or more of the ingredients. Accordingly, the pharmaceutical compositions encompass any composition made by admixing the active ingredient, active ingredient dispersion or composite, additional active ingredient(s), and pharmaceutically acceptable excipients.

Following examples are given by way of illustration therefore should not be construed to limit the scope of the invention.

EXAMPLES

Example 1: General Procedure for the Synthesis of Unsaturated γ-Spiroketal-γ-Lactones from Alkynols and α-Ketoesters To the alkynol (0.66 mmol) and α-ketoester (0.66 mmol) in 5 mL of anhydrous $CH_2Cl_2$ in a dry round bottom flask, was added $Bi(OTf)_3$ (0.13 mmol) under argon atmosphere at 27° C. and stirred the reaction mixture at 27° C. for mentioned reaction time. After completion of reaction (typically after 12-48 h, monitored by TLC, visualized using UV, anisaldehyde, and $KMnO_4$ staining solutions), the reaction mixture was quenched with saturated aqueous solution of sodium bicarbonate ($NaHCO_3$) then extracted with $CH_2Cl_2$ (2×10 mL). The combined organic layers were dried over anhydrous sodium sulphate and filtered through sintered glass funnel. The residue was concentrated under reduced pressure and purified by silica gel column chromatography (100-200 mesh) to afford the corresponding unsaturated γ-spiroketal-γ-lactone.

A. Synthesis of 3-Methyl-1, 14-dioxadispiro [4.1.5$^7$.2$^5$] tetradec-3-en-2-one (1)

Following the General Procedure, to the mixture of (1-(prop-2-yn1 yl) cyclohexyl) methanol (0.100 g, 0.66 mmol) and ethyl pyruvate (0.104 g, 0.66 mmol) in anhydrous $CH_2Cl_2$ (5 mL) was add $Bi(OTf)_3$ (0.090 g, 0.13 mmol) under argon atmosphere at 27° C. and stirred the reaction mixture for 12 h at 27° C. Purification of the crude product by column chromatography ($SiO_2$, 5% EtOAc/hexanes) afforded 3-methyl-1, 14-dioxadispiro [4.1.5$^7$.2$^5$] tetradec-3-en-2-one (0.117 g, 80%). TLC: $R_f$=0.40 ($SiO_2$, 20% EtOAc/hexanes); $^1$H NMR ($CDCl_3$, 400 MHz): δ 6.74-6.65 (m, 1H), 3.95 (d, J=8.8 Hz, 1H), 3.86 (d, J=8.3 Hz, 1H), 2.12 (d, J=13.7 Hz, 1H), 2.01 (d, J=14.2 Hz, 1H), 1.91 (d, J=0.98 Hz, 3H), 1.77-1.64 (m, 2H), 1.57-1.36 (m, 8H); $^{13}$C NMR ($CDCl_3$, 101 MHz): δ 171.6, 145.1, 132.5, 113.2, 80.4, 47.1, 43.6, 37.4, 35.5, 25.5, 23.8, 23.7, 10.4; FIRMS (ESI) m/z calcd for $C_{13}H_{19}O_3$ $[M+H]^+$ 223.1329, found 223.1326.

B. Synthesis of 3-Phenyl-1, 14-dioxadispiro [4.4.5$^7$.2$^5$] tetradec-3-en-one (2)

Following the General Procedure, to the mixture of (1-(prop-2-yn-1-yl) cyclohexyl) methanol (0.100 g, 0.66 mmol) and ethyl phenylglyoxylate (0.104 g, 0.66 mmol) in anhydrous $CH_2Cl_2$ (5 mL) was added $Bi(OTf)_3$ (0.09 g, 0.13 mmol) under argon atmosphere at 27° C. and stirred the reaction mixture for 12 h. Purification of the crude product by column chromatography ($SiO_2$, 2% EtOAc/hexanes) afforded 3-phenyl-1,14-dioxadispiro[4.4.5$^7$.2$^5$]tetradec-3-en-one as a crystalline solid (0.142 g, 76%). TLC: $R_f$=0.75 ($SiO_2$, 20% EtOAc/hexanes); $^1$H NMR ($CDCl_3$, 400 MHz): δ 7.89-7.79 (m, 2H), 7.42 (d, J=3.7 Hz, 3H), 7.18 (s, 1H), 4.03 (d, J=7.9 Hz, 1H), 3.94 (d, J=8.5 Hz, 1H), 2.20 (dd, J=36.01, 13.4 Hz, 2H), 1.81-1.69 (m, 2H), 1.62-1.38 (m, 8H); $^{13}$C NMR ($CDCl_3$, 101 MHz): δ 169.3, 143.7, 133.6, 129.7, 129.0, 128.7, 127.5, 112.4, 80.5, 47.4, 43.8, 37.4, 35.5, 25.6, 23.9, 23.8; HRMS (ESI) m/z calcd for $C_{18}H_{21}O_3$ $[M+H]^+$ 285.1485, found 285.1483.

C. Synthesis of 3-(4-Methoxyphenyl)-1, 14-dioxadispiro [4.1.5$^7$.2$^5$] tetradec-3-en-2-one (3)

Following the General Procedure, to the mixture of (1-(prop-2-yn-1-yl) cyclohexyl) methanol (0.05 g, 0.33 mmol) and ethyl anisylglyoxylate (0.054 g, 0.33 mmol) in anhydrous $CH_2Cl_2$ (3 mL) was added $Bi(OTf)_3$ (0.045 g, 0.066 mmol) under argon atmosphere at 27° C. and stirred the reaction mixture for 12 h. Purification of the crude product by column chromatography ($SiO_2$, 5% EtOAc/hexanes) afforded 3-(4-methoxyphenyl)-1, 14-dioxadispiro [4.1.5$^7$.2$^5$] tetradec-3-en-2-one (0.06 g, 72%). TLC: $R_f$=0.75 ($SiO_2$, 20% EtOAc/hexanes); $^1$H NMR ($CDCl_3$, 400 MHz): δ 7.81 (d, J=8.8 Hz, 2H), 7.05 (s, 1H), 6.93 (d, J=8.8 Hz, 2H), 4.01 (d, J=8.3 Hz, 1H), 3.92 (d, J=8.3 Hz, 1H), 3.84 (s, 3H), 2.16 (dd, J=38.15, 13.7 Hz, 2H), 1.77-1.69 (m, 2H), 1.59-1.40 (m, 8H); $^{13}$C NMR ($CDCl_3$, 101 MHz): δ 169.6, 160.7, 141.3, 132.9, 129.0, 121.5, 114.1, 112.4, 80.5, 55.3, 47.4, 43.8, 37.4, 35.5, 25.6, 23.9, 23.8; HRMS (ESI) m/z calcd for $C_{19}H_{23}O_4$ $[M+H]^+$ 315.1591, found 315.1588.

D. Synthesis of 3-(p-Tolyl)-1, 14-dioxadispiro [4.1.5$^7$.2$^5$] tetradec-3-en-2-one (4)

Following the General Procedure, to the reaction mixture of (1-(prop-2-yn-1-yl) cyclohexyl) methanol (0.05 g, 0.32 mmol) and ethyl p-tolylglyoxylate (0.063 g, 0.32 mmol) in anhydrous $CH_2Cl_2$ (4 mL) was added $Bi(OTf)_3$ (0.042 g, 0.064 mmol) under argon atmosphere at 27° C. and stirred the reaction mixture for 12 h. Purification of crude product by column chromatography ($SiO_2$, 2% EtOAc/hexanes) afforded 3-(p-tolyl)-1, 14-dioxadispiro [4.1.5$^7$.2$^5$] tetradec-3-en-2-one (0.067 g, 70%) as a crystalline solid. TLC: $R_f$=0.60 ($SiO_2$, 20% EtOAc/hexanes); $^1$H NMR ($CDCl_3$, 500 MHz): δ 7.75 (d, J=8.01 Hz, 2H), 7.22 (d, J=8.01 Hz, 2H), 7.12 (s, 1H), 4.02 (d, J=8.4 Hz, 1H), 3.93 (d, J=8.4 Hz, 1H), 2.38 (s, 3H), 2.23 (d, J=14.11 Hz, 1H), 2.13 (d, J=13.73 Hz, 1H), 1.78-1.68 (m, 2H), 1.61-1.31 (m, 8H); $^{13}$C NMR ($CDCl_3$, 126 MHz): δ 169.4, 142.7, 139.9, 133.5, 129.4, 127.4, 126.1, 112.3, 80.5, 43.8, 37.4, 35.6, 25.6, 23.9, 23.8, 21.4; HRMS (ESI) m/z calcd for $C_{19}H_{23}O_3$ $[M+H]^+$ 299.1642 found 299.1634.

E. Synthesis of 3-Methyl-1, 13-dioxadispiro [4.1.4$^7$.2$^5$] tridec-3-en-2-one (5)

Following the General Procedure, to the mixture of (1-(prop-2-yn-1-yl)cyclopentyl)methanol (0.1 g, 0.72 mmol) and ethylpyruvate (0.083 g, 0.72 mmol) in anhydrous $CH_2Cl_2$ (5 mL) was added $Bi(OTf)_3$ (0.09 g, 0.144 mmol) under argon atmosphere at 27° C. and stirred the reaction mixture for 12 h. Purification of the crude product by column chromatography (SiO$_2$, 5% EtOAc/hexanes) afforded 3-methyl-1,13-dioxadispiro[4.1.4$^7$.2$^5$]tridec-3-en-2-one (0.117 g, 78%) as a white solid. TLC: R$_f$=0.3 (SiO$_2$, 20% EtOAc/hexanes); $^1$H NMR (CDCl$_3$, 500 MHz): δ 6.72-6.69 (m, 1H), 4.01 (d, J=8.4 Hz, 1H), 3.85 (d, J=8.4 Hz, 1H), 2.18 (s, 2H), 1.92 (d, J=1.14 Hz, 3H), 1.86-1.81 (m, 2H), 1.74-1.58 (m, 6H); $^{13}$C NMR (CDCl$_3$, 126 MHz): δ 171.6, 145.2, 132.5, 113.3, 81.1, 50.3, 47.4, 38.0, 37.2, 24.6, 24.4, 10.4; HRMS (ESI): calcd for C$_{12}$H$_{17}$O$_3$ [M+H]$^+$ 209.1172, found 209.1171.

F. Synthesis of 3-Phenyl-1, 13-dioxadispiro [4.1.4$^7$.2$^5$] tridec-3-en-one (6)

Following the General Procedure, to the mixture of (1-(prop-2-yn-1-yl) cyclopentyl) methanol (0.1 g, 0.72 mmol) ethyl phenylglyoxylate (0.128 g, 0.72 mmol) in anhydrous CH$_2$Cl$_2$ (6 mL) was added Bi(OTf)$_3$ (0.09 g, 0.144 mmol) under argon atmosphere at 27° C. and stirred the reaction mixture for 12 h. Purification of the crude product by column chromatography (SiO$_2$, 5% EtOAc/hexanes) afforded 3-phenyl-1,13-dioxadispiro[4.1.4$^7$.2$^5$]tridec-3-en-one (0.136 g, 70%). TLC: R$_f$=0.5 (SiO$_2$, 20% EtOAc/hexanes); $^1$H NMR (CDCl$_3$, 500 MHz): δ 7.87-7.81 (m, 2H), 7.45-7.39 (m, 3H), 7.19 (s, 1H), 4.08 (d, J=8.0 Hz, 1H), 3.92 (d, J=8.0 Hz, 1H), 2.31 (dd, J=17.55, 13.73 Hz, 2H), 1.91-1.87 (m, 2H), 1.79-1.63 (m, 6H); $^{13}$C NMR (CDCl$_3$, 126 MHz): δ 169.3, 143.7, 133.6, 129.7, 129.0, 128.7, 127.5, 112.4, 81.2, 50.5, 47.7, 38.0, 37.2, 24.7, 24.4; HRMS (ESI): calcd for C$_{17}$H$_{19}$O$_3$ [M+H]$^+$ 271.1329, found 271.1328.

G. Synthesis of 3-(4-Methoxyphenyl)-1, 13-dioxadispiro [4.1.4$^7$.2$^5$] tridec-3-en-2-one (7)

Following the General Procedure, to the reaction mixture of (1-(prop-2-yn-1-yl) cyclopentyl) methanol (0.1 g, 0.72 mmol) and ethyl anisylglyoxylate (0.15 g, 0.72 mmol) in anhydrous CH$_2$Cl$_2$ (2 mL) was added Bi(OTf)$_3$ (0.094 g, 0.14 mmol) under argon atmosphere at 27° C. and stirred the reaction mixture for 12 h. Purification of crude product by column chromatography (SiO$_2$, 8% EtOAc/hexanes) afforded 3-(4-methoxyphenyl)-1,13-dioxadispiro[4.1.4$^7$.2$^5$] tridec-3-en-2-one crystalline solid (0.151 g, 70%). TLC: R$_f$=0.60 (SiO$_2$, 20% EtOAc/hexanes); $^1$H NMR (CDCl$_3$, 500 MHz): δ 7.88-7.80 (m, 2H), 7.06 (s, 1H), 6.96-6.91 (m, 2H), 4.07 (d, J=8.01 Hz, 1H), 3.91 (d, J=8.01 Hz, 1H), 3.84 (s, 3H), 2.29 (dd, J=13.35, 3.43 Hz, 2H), 1.91-1.85 (m, 2H), 1.78-1.63 (m, 6H); $^{13}$C NMR (126 MHz, CDCl$_3$): δ 169.6, 160.7, 141.3, 132.9, 129.0, 121.6, 114.1, 112.4, 81.2, 55.3, 50.5, 47.7, 38.1, 37.2, 29.7, 24.7, 24.4; HRMS (ESI) m/z calcd for C$_{18}$H$_{21}$O$_4$ [M+H]$^+$ 300.1434 found 301.1425.

H. Synthesis of 3-(p-Tolyl)-1, 13-Dioxadispiro [4.1.4$^7$.2$^5$] Tridec-3-En-2-One (8)

Following the General Procedure, to the reaction mixture of (1-(prop-2-yn-1-yl) cyclopentyl) methanol (0.05 g, 0.36 mmol) and ethyl p-tolylglyoxylate (0.069 g, 0.36 mmol) in anhydrous CH$_2$Cl$_2$ (3 mL) was added Bi(OTf)$_3$ (0.042 g, 0.072 mmol) under argon atmosphere at 27° C. and stirred the reaction mixture for 12 h. Purification of crude product by column chromatography (SiO$_2$, 2% EtOAc/hexanes) afforded 3-(p-tolyl)-1,13-dioxadispiro[4.1.4$^7$.2$^5$]tridec-3-en-2-one (0.073 g, 72%) as a white solid. TLC: R$_f$=0.60 (SiO$_2$, 20% EtOAc/hexanes); $^1$H NMR (CDCl$_3$, 400 MHz): δ 7.75 (d, J=8.5 Hz, 2H), 7.22 (d, J=7.9 Hz, 2H), 7.13 (s, 1H), 4.07 (d, J=8.5 Hz, 1H), 3.91 (d, J=7.9 Hz, 1H), 2.39 (s, 3H), 2.29 (dd, J=14.404, 1.22 Hz, 2H), 1.93-1.85 (m, 2H), 1.80-1.61 (m, 6H); $^{13}$C NMR (CDCl$_3$, 101 MHz): δ 169.4, 142.7, 139.9, 133.4, 129.4, 127.4, 126.1, 112.4, 81.2, 50.5, 47.7, 38.0, 37.2, 24.7, 24.4, 21.4; HRMS (ESI) m/z calcd for C$_{18}$H$_{21}$O$_3$ [M+H]$^+$ 285.1485 found 285.1476.

I. Synthesis of 3-(4-Nitrophenyl)-1, 13-dioxadispiro [4.1.4$^7$.2$^5$] tridec-3-en-2 one (9)

Following the General Procedure, to the mixture of (1-(prop-2-yn-1-yl) cyclopentyl) methanol (0.112 g, 0.811 mmol) and ethyl 2-(4-nitrophenyl)-2-oxoacetate (0.181 g, 0.811 mmol) in anhydrous CH$_2$Cl$_2$ (5 mL) was added Bi(OTf)$_3$ (0.106 g, 0.162 mmol) at 27° C. under argon atmosphere and stirred the reaction mixture for 12 h. Quenched with aqueous NaHCO$_3$ solution (5 mL), stirred for 5 min then extracted with CH$_2$Cl$_2$ (2×5 mL), dried over anhydrous Na$_2$SO$_4$, filtered and concentrated. Resulting solid was dissolved in hexanes (5 mL) and slowly added the minimum amount of CH$_2$Cl$_2$. The resulting solution was stand at 27° C. until all solvents were evaporated to form crystalline product 3-(4-nitrophenyl)-1,13-dioxadispiro [4.1.4$^7$.2$^5$]tridec-3-en-2-one (0.144 g, 78%). TLC: R$_f$=0.75 (SiO$_2$, 20% EtOAc/hexanes); $^1$H NMR (CDCl$_3$, 400 MHz): δ 8.28 (d, J=8.5 Hz, 2H), 8.05 (d, J=9.2 Hz, 2H), 7.38 (s, 1H), 4.10 (d, J=8.5 Hz, 1H), 3.94 (d, J=7.9 Hz, 1H), 2.39-2.27 (m, 2H), 1.95-1.83 (m, 2H), 1.81-1.62 (m, 6H); $^{13}$C NMR (CDCl$_3$, 101 MHz): δ 168.3, 148.3, 147.0, 135.0, 131.7, 128.5, 123.9, 112.6, 81.5, 50.6, 47.6, 37.9, 37.1, 24.7, 24.4; HRMS (ESI) m/z calcd for C$_{17}$H$_{18}$O$_5$N [M+H]$^+$ 316.1179, found 316.1171.

J. Synthesis of 3-Methyl-1, 6-dioxaspiro [4.4] non-3-en-2-one (10)

Following the General Procedure, to the reaction mixture of pent-4-yn-1-ol (0.1 g, 1.1 mmol) and ethyl pyruvate (0.137 g, 1.1 mmol) in anhydrous CH$_2$Cl$_2$ (5 mL) was added Bi(OTf)$_3$ (0.154 g, 0.22 mmol) under argon atmosphere at 27° C. and stirred the reaction mixture for 48 h purification of crude product by column chromatography (SiO$_2$, 5% EtOAc/hexanes) afforded 3-methyl-1,6-dioxaspiro[4.4]non-3-en-2-one (0.106 g, 58%) as a yellow oily liquid. TLC: R$_f$=0.60 (SiO$_2$, 20% EtOAc/hexanes); $^1$H NMR (CDCl$_3$, 500 MHz): δ 6.73-6.70 (m, 1H), 4.65-4.19 (m, 1H), 4.10-4.03 (m, 1H), 2.34-2.23 (m, 1H), 2.22-2.06 (m, 3H), 1.93 (d, J=1.91 Hz, 3H); $^{13}$C NMR (CDCl$_3$, 126 MHz): δ 171.4, 144.4, 133.3, 112.7, 70.3, 35.3, 24.2, 10.5; HRMS (ESI) m/z calcd for C$_8$H$_{11}$O$_3$ [M+H]$^+$ 154.0703 found 155.0699.

K. Synthesis of 3-Phenyl-1, 6-dioxaspiro [4, 4] non-3-en-2-one (11)

Following the General Procedure, to the mixture of 4-pentyne-1-ol (0.1 g, 1.19 mmol) and ethyl phenylglyoxylate (0.21 g, 1.19 mmol) in anhydrous CH$_2$Cl$_2$ (5 mL) was added Bi(OTf)$_3$ (0.249 g, 0.238 mmol) under argon atmosphere at 27° C. and stirred the reaction mixture for 48 h at 27° C. Purification of the crude product by column chromatography (SiO$_2$, 5% EtOAc/hexane) afforded 3-phenyl-1, 6-dioxaspiro [4, 4] non-3-en-2-one (0.138 g, 54%). TLC: R$_f$=0.45 (SiO$_2$, 20% EtOAc/hexanes); $^1$H NMR (CDCl$_3$, 400 MHz): δ 7.90-7.80 (m, 2H), 7.49-7.34 (m, 3H), 7.21 (s, 1H), 4.28 (td, J=8.2, 3.7 Hz, 1H), 4.11 (q, J=7.5 Hz, 1H), 2.42-2.14 (m, 4H); $^{13}$C NMR (CDCl$_3$, 101 MHz): δ 169.2, 143.1, 134.3, 129.8, 129.0, 128.7, 128.2, 128.1, 127.7, 127.5, 127.3,

L. Synthesis of 3-(4-Methoxyphenyl)-1, 6-dioxaspiro [4, 4] non-3-en-2-one (12)

Following the General Procedure, to the mixture of 4-pentyne-1-ol (0.3 g, 3.57 mmol) and ethyl anisylglyoxylate (0.743 g, 3.57 mmol) in anhydrous $CH_2Cl_2$ (6 mL) was added $Bi(OTf)_3$ (0.465 g, 0.714 mmol) under argon atmosphere at 27° C. and stirred the reaction mixture for 48 h at 27° C. Purification of the crude product by column chromatography ($SiO_2$, 5% EtOAc/hexanes) afforded 3-(4-methoxyphenyl)-1,6-dioxaspiro[4,4]non-3-en-2-one (3cc) (0.46 g, 52%). TLC: $R_f$=0.40 ($SiO_2$, 20% EtOAc/hexanes); $^1$H NMR (CDCl$_3$, 500 MHz): δ 7.82 (d, J=8.8 Hz, 2H), 7.07 (s, 1H), 6.92 (d, J=8.8 Hz, 2H), 4.31-4.24 (m, 1H), 4.15-4.08 (m, 1H), 3.83 (s, 3H), 2.38-2.12 (m, 4H); $^{13}$C NMR (CDCl$_3$, 126 MHz): δ 169.5, 160.8, 140.5, 133.7, 129.0, 121.6, 114.1, 111.9, 70.4, 55.3, 35.7, 24.3; HRMS (ESI): calcd for $C_{14}H_{15}O_4$ [M+H]$^+$ 247.0965, found 247.0964.

M. Synthesis of 3-(p-Tolyl)-1,6-Dioxaspiro[4.4] Non-3-En-2-One (13)

Following the General Procedure, to the reaction mixture of pent-4-yn-1-ol (0.1 g, 1.1 mmol) and ethyl p-tolylglyoxylate (0.228 g, 1.1 mmol) in anhydrous $CH_2Cl_2$ (5 mL) was added $Bi(OTf)_3$ (0.154 g, 0.22 mmol) under argon atmosphere at 27° C. and stirred the reaction mixture for 48 h. Purification of crude product by column chromatography ($SiO_2$, 8% EtOAc/hexanes) afforded 3-(p-tolyl)-1, 6-dioxaspiro [4.4] non-3-en-2-one crystalline solid (0.084 g, 62%). TLC: $R_f$=0.60 ($SiO_2$, 20% EtOAc/hexanes); $^1$H NMR (CDCl$_3$, 400 MHz): δ 7.76 (d, J=7.9 Hz, 2H), 7.23 (d, J=7.9 Hz, 2H), 7.15 (s, 1H), 4.33-4.25 (m, 1H), 4.17-4.08 (m, 1H), 2.38 (s, 3H), 2.43-2.12 (m, 4H); $^{13}$C NMR (CDCl$_3$, 101 MHz): δ 169.3, 141.9, 140.0, 134.2, 129.4, 127.4, 126.2, 111.8, 70.4, 35.7, 24.3, 21.4; FIRMS (ESI) m/z calcd for $C_{14}H_{15}O_3$ [M+H]$^+$ 230.1016 found 231.1009.

N. Synthesis of 3, 4-Dimethyl-1, 14-dioxadispiro [4.1.5$^7$.2$^5$] tetradec-3-en-2-one (14)

Following the General Procedure, to the mixture of (1-(but-2-yn-1-yl) cyclohexyl) methanol (0.05 g, 0.3 mmol) and ethyl pyruvate (0.05 g, 0.3 mmol) in anhydrous $CH_2Cl_2$ (3 mL) was added $Bi(OTf)_3$ (0.04 g, 0.06 mmol) under argon atmosphere at 27° C. and stirred the reaction n mixture for 12 h at 27° C. Purification of the crude product by silica gel column chromatography ($SiO_2$, 5% EtOAc/hexanes) gave 3, 4-dimethyl-1, 14-dioxadispiro [4.1.5$^7$.2$^5$] tetradec-3-en-2-one (0.046 g, 65%) as a yellow oil. TLC: $R_f$=0.7 ($SiO_2$, 20% EtOAc/hexanes); $^1$H NMR (CDCl$_3$, 500 MHz): δ 3.95 (d, J=8.8 Hz, 1H), 3.85 (d, J=8.8 Hz, 1H), 2.04-1.94 (m, 2H), 1.90 (s, 3H), 1.80 (s, 3H), 1.72-1.65 (m, 2H), 1.53-1.39 (m, 8H); $^{13}$C NMR (CDCl$_3$, 126 MHz): δ 171.7, 154.9, 126.0, 114.5, 80.6, 45.7, 43.4, 37.4, 35.6, 25.5, 23.8, 23.7, 10.5, 8.6; HRMS (ESI) m/z calcd for $C_{14}H_{21}O_3$ [M+H]$^+$ 237.1485, found 237.1486.

O. Synthesis of 4-Methyl-3-phenyl-1, 14-dioxadispiro [4.1.5$^7$.2$^5$] tetradec-3-en-2-one (15)

Following the General Procedure, to the mixture of (1-(but-2-yn-1-yl) cyclohexyl) methanol (0.05 g, 0.3 mmol) and ethyl phenylglyoxylate (0.054 g, 0.3 mmol) in dry $CH_2Cl_2$ (3 mL) was added $Bi(OTf)_3$ (0.04 g, 0.066 mmol) under argon atmosphere at 27° C. and stirred the reaction mixture for 12 h. Purification of the crude product by column chromatography ($SiO_2$, 3% EtOAc/hexanes) afforded 4-methyl-3-phenyl-1, 14-dioxadispiro[4.1.5$^7$.2$^5$] tetradec-3-en-2-one (6ab) (0.062 g, 68%) as a crystalline solid. TLC: $R_f$=0.5 ($SiO_2$, 20% EtOAc/hexanes). $^1$H NMR (CDCl$_3$, 400 MHz): δ 7.53-7.34 (m, 5H), 4.06 (d, J=8.5 Hz, 1H), 3.95 (d, J=7.9 Hz, 1H), 2.23-2.05 (m, 2H), 2.13 (s, 3H), 1.83-1.72 (m, 2H), 1.60-1.45 (m, 8H); $^{13}$C NMR (CDCl$_3$, 101 MHz): δ 169.9, 156.0, 129.6, 129.0, 128.98, 128.7, 128.5, 113.9, 80.9, 46.1, 43.7, 37.4, 35.6, 25.5, 23.9, 23.8, 11.5; HRMS (ESI) m/z calcd for $C_{19}H_{23}O_3$ [M+H]$^+$ 299.1642, found 299.1643.

P. Synthesis of 3-(4-Methoxyphenyl)-4-methyl-1, 14-dioxadispiro [4.1.5$^7$.2$^5$] tetradec-3-en-2-one (16)

Following the General Procedure, to the mixture of (1-(but-2-yn-1-yl) cyclohexyl) methanol (0.050 g, 0.3 mmol) and ethyl anisylglyoxylate (0.063 g, 0.3 mmol) in anhydrous $CH_2Cl_2$ (3 mL) was added $Bi(OTf)_3$ (0.04 g, 0.066 mmol) under argon atmosphere at 27° C. and stirred the reaction mixture for 12 h. Purification of the crude product by column chromatography ($SiO_2$, 5% EtOAc/hexanes) afforded 3-(4-methoxyphenyl)-4-methyl-1, 14-dioxadispiro [4.1.5$^7$.2$^5$] tetradec-3-en-2-one (0.062 g, 62%) as a crystalline solid. TLC: $R_f$=0.45 ($SiO_2$, 20% EtOAc/hexanes); $^1$H NMR (CDCl$_3$, 400 MHz): δ 7.46 (d, J=8.5 Hz, 2H), 6.97 (d, J=8.5 Hz, 2H), 4.05 (d, J=7.9 Hz, 1H), 3.94 (d, J=8.5 Hz, 1H), 3.85 (s, 3H), 2.12 (s, 3H), 2.21-2.04 (m, 2H), 1.76-1.7 (m, 2H), 1.61-1.41 (m, 8H); $^{13}$C NMR (CDCl$_3$, 101 MHz): δ 170.2, 159.8, 154.3, 130.4, 128.4, 122.0, 113.9, 80.8, 55.3, 46.1, 43.6, 37.4, 35.7, 25.6, 23.9, 23.8, 11.6; HRMS (ESI) m/z calcd for $C_{20}H_{25}O_4$ [M+H]$^+$ 329.1747, found 329.1739.

Q. Synthesis of 4-Methyl-3-(p-tolyl)-1, 14-dioxadispiro [4.1.5$^7$.2$^5$] tetradec-3-en-2-one (17)

Following the General Procedure, to the mixture of (1-(but-2-yn-1-yl) cyclohexyl) methanol (0.05 g, 0.3 mmol) and ethyl p-tolylglyoxylate (0.058 g, 0.3 mmol) in anhydrous $CH_2Cl_2$ (3 mL) was added $Bi(OTf)_3$ (0.04 g, 0.066 mmol) under argon atmosphere at 27° C. and stirred the reaction mixture for 12 h. Purification of the crude product by silica gel column chromatography (Si $O_2$, 4% EtOAc/hexanes) gave 4-methyl-3-(p-tolyl)-1, 14-dioxadispiro [4.1.5$^7$.2$^5$] tetradec-3-en-2-one (0.068 g, 72%) as a crystalline solid. TLC: $R_f$=0.45 ($SiO_2$, 20% EtOAc/hexanes); $^1$H NMR (CDCl$_3$, 400 MHz): δ 7.40 (d, J=7.9 Hz, 2H), 7.26 (d, J=7.9 Hz, 2H), 4.06 (d, J=8.5 Hz, 1H), 3.94 (d, J=8.5 Hz, 1H), 2.40 (s, 3H), 2.12 (s, 3H), 2.21-2.05 (m, 2H), 1.81-1.72 (m, 2H), 1.56-1.34 (m, 8H); $^{13}$C NMR (CDCl$_3$, 101 MHz): δ 170.0, 155.1, 138.7, 129.2, 128.9, 126.7, 113.9, 80.8, 77.2, 46.1, 43.6, 37.4, 35.7, 25.6, 23.9, 23.8, 21.4, 11.5; HRMS (ESI) m/z calcd for $C_{20}H_{25}O_3$ [M+H]$^+$ 313.1798, found 313.1808.

R. Synthesis of 4-Ethyl-3-methyl-1, 14-dioxadispiro [4.1.5$^7$.2$^5$] tetradec-3-en-2-one (18)

Following the General Procedure, to the mixture of (1-(pent-2-yn-1-yl) cyclohexyl) methanol (0.1 g, 0.55 mmol) and ethyl pyruvate (0.064 g, 0.55 mmol) in anhydrous $CH_2Cl_2$ (3 mL) was added $Bi(OTf)_3$ (0.073 g, 0.11 mmol) under argon atmosphere at 27° C. and stirred the reaction mixture for 12 h. Purification of the crude product by silica gel column chromatography (SiO$_2$, 5% EtOAc/hexanes) provided 4-ethyl-3-methyl-1, 14-dioxadispiro [4.1.5$^7$.2$^5$] tetradec-3-en-2-one (0.093 g, 68%) as a colorless oil. TLC: R$_f$=0.45 (SiO$_2$, 20% EtOAc/hexanes); $^1$H NMR (CDCl$_3$, 400 MHz): δ 3.96 (d, J=8.5 Hz, 1H), 3.86 (d, J=7.9 Hz, 1H), 2.44-2.31 (m, 1H), 2.31-2.2 (m, 1H), 2.06-1.96 (m, 2H), 1.84 (s, 3H), 1.74-1.67 (m, 2H), 1.55-1.39 (m, 8H), 1.17 (t, J=7.6 Hz, 3H); $^{13}$C NMR (CDCl$_3$, 101 MHz): δ 171.9, 159.4, 126.0, 114.9, 80.5, 45.9, 43.3, 37.6, 35.7, 25.5, 23.9, 23.7, 18.9, 12.3, 8.6; HRMS (ESI) m/z calcd for C$_{15}$H$_{23}$O$_3$ [M+H]$^+$ 251.1642, found 251.1644.

S. Synthesis of 4-Ethyl-3-phenyl-1, 14-dioxadispiro [4.1.5$^7$.2$^5$] tetradec-3-en-2-one (19)

Following the General Procedure, to the mixture of (1-(pent-2-yn-1-yl) cyclohexyl) methanol (0.1 g, 0.55 mmol) and ethyl phenylglyoxylate (0.099 g, 0.55 mmol) in anhydrous CH$_2$Cl$_2$ (3 mL) was added Bi(OTf)$_3$ (0.073 g, 0.11 mmol) under argon atmosphere at 27° C. and stirred the reaction mixture for 12 h. Purification of the crude product by silica gel column chromatography (SiO$_2$, 3% EtOAc/hexanes) afforded 4-ethyl-3-phenyl-1, 14-dioxadispiro [4.1.5$^7$.2$^5$] tetradec-3-en-2-one (0.122 g, 70%) as a solid. TLC: R$_f$=0.5 (SiO$_2$, 20% EtOAc/hexanes); $^1$H NMR (CDCl$_3$, 500 MHz): δ 7.55-7.34 (m, 5H), 4.06 (d, J=8.4 Hz, 1H), 3.95 (d, J=8.4 Hz, 1H), 2.68-2.58 (m, 1H), 2.46-2.37 (m, 1H), 2.18 (s, 2H), 1.81-1.74 (m, 2H), 1.62-1.43 (m, 8H), 1.18 (t, J=7.6 Hz, 3H); $^{13}$C NMR (CDCl$_3$, 126 MHz): δ 170.1, 160.5, 129.8, 129.4, 129.1, 128.9, 128.7, 128.4, 114.6, 80.7, 46.3, 43.5, 37.6, 35.7, 25.6, 23.9, 23.8, 19.4, 12.5; FIRMS (ESI) m/z calcd for C$_{20}$H$_{25}$O$_3$ [M+H]$^+$ 313.1798, found 313.1797.

T. Synthesis of 4-Ethyl-3-(4-methoxyphenyl)-1, 14-dioxadispiro [4.1.5$^7$.2$^5$] tetradec-3-en-2-one (20)

Following the General Procedure, to the mixture of (1-(pent-2-yn-1-yl) cyclohexyl) methanol (0.1 g, 0.55 mmol) and ethyl anisylglyoxylate (0.114 g, 0.55 mmol) in anhydrous CH$_2$Cl$_2$ (5 mL) was added Bi(OTf)$_3$ (0.073 g, 0.11 mmol) under argon atmosphere at 27° C. and stirred the reaction mixture for 12 h. Purification of the crude product by silica gel column chromatography (SiO$_2$, 2% EtOAc/hexanes) gave 4-ethyl-3-(4-methoxyphenyl)-1, 14-dioxadispiro [4.1.5$^7$.2$^5$] tetradec-3-en-2-one (0.146 g, 72%) as a solid. TLC: R$_f$=0.5 (SiO$_2$, 20% EtOAc/hexanes); $^1$H NMR (CDCl$_3$, 400 MHz): δ 7.44 (d, J=8.5 Hz, 2H), 6.96 (d, J=8.5 Hz, 2H), 4.03 (d, J=8.5 Hz, 1H), 3.93 (d, J=8.5 Hz, 1H), 3.84 (s, 3H), 2.69-2.54 (m, 1H), 2.47-2.32 (m, 1H), 2.15 (s, 2H), 1.82-1.71 (m, 2H), 1.60-1.41 (m, 8H), 1.18 (t, J=7.6 Hz, 3H); $^{13}$C NMR (CDCl$_3$, 101 MHz): δ 170.4, 159.8, 159.0, 130.2, 128.7, 122.2, 114.5, 113.9, 80.6, 55.3, 46.3, 43.4, 37.6, 35.7, 25.6, 23.9, 23.8, 19.4, 12.5; HRMS (ESI) m/z calcd for C$_{21}$H$_{27}$O$_4$ [M+H]$^+$ 343.1904, found 343.1905.

U. Synthesis of 4-Ethyl-3-(p-tolyl)-1, 14-dioxadispiro [4.1.5$^7$.2$^5$] tetradec-3-en-2-one (21)

Following the General Procedure, to the mixture of (1-(pent-2-yn-1-yl) cyclohexyl) methanol (0.1 g, 0.55 mmol) and ethyl p-tolylglyoxylate (0.106 g, 0.55 mmol) in anhydrous CH$_2$Cl$_2$ (5 mL) was added Bi(OTf)$_3$ (0.073 g, 0.11 mmol) under argon atmosphere at 27° C. and stirred the reaction mixture for 12 h. Purification of the crude product by silica gel column chromatography (SiO$_2$, 2% EtOAc/hexanes) afforded 4-ethyl-3-(p-tolyl)-1, 14-dioxadispiro [4.1.5$^7$.2$^5$] tetradec-3-en-2-one (0.13 g, 76%) as a solid. TLC: R$_f$=0.6 (SiO$_2$, 20% EtOAc/hexanes); $^1$H NMR (CDCl$_3$, 500 MHz): δ 7.38 (d, J=8.4 Hz, 2H), 7.25 (d, J=7.6 Hz, 2H), 4.05 (d, J=8.4 Hz, 1H), 3.95 (d, J=8.8 Hz, 1H), 2.68-2.58 (m, 1H), 2.4 (s, 3H), 2.46-2.36 (m, 1H), 2.17 (s, 2H), 1.81-1.74 (m, 2H), 1.63-1.43 (m, 8H), 1.19 (t, J=7.6 Hz, 3H); $^{13}$C NMR (CDCl$_3$, 126 MHz): δ 170.3, 159.8, 138.7, 129.3, 129.2, 128.8, 127.3, 126.9, 114.5, 80.6, 46.3, 43.4, 37.6, 35.8, 25.6, 23.9, 23.8, 21.3, 19.4, 12.5; HRMS (ESI) m/z calcd for C$_{21}$H$_{27}$O$_3$ [M+H]$^+$ 327.1955, found 327.1959.

V. Synthesis of 3-Methyl-4-phenyl-1, 14-dioxadispiro [4.1.5$^7$.2$^5$] tetradec-3-en-2-one (22)

Following the General Procedure, to the mixture of (1-(3-phenylprop-2-yn-1-yl) cyclohexyl) methanol (0.1 g, 0.43 mmol) and ethyl pyruvate (0.052 g, 0.43 mmol) in anhydrous CH$_2$Cl$_2$ (5 mL) was added Bi(OTf)$_3$ (0.057 g, 0.086 mmol) under argon atmosphere at 27° C. and stirred the reaction mixture for 12 h. Purification of the crude product by silica gel column chromatography (SiO$_2$, 3% EtOAc/hexanes) afforded 3-methyl-4-phenyl-1, 14-dioxadispiro [4.1.5$^7$.2$^5$] tetradec-3-en-2-one (0.097 g, 74%) as a white solid. TLC: R$_f$=0.60 (SiO$_2$, 20% EtOAc/hexanes); $^1$H NMR (CDCl$_3$, 500 MHz): δ 7.56-7.40 (m, 5H), 4.09 (d, J=8.5 Hz, 1H), 3.94 (d, J=8.5 Hz, 1H), 2.09 (d, J=14.0 Hz, 1H), 2.0 (s, 3H), 1.86 (d, J=14.0 Hz, 1H), 1.78-1.71 (m, 2H), 1.54-1.44 (m, 2H), 1.42-1.29 (m, 6H); $^{13}$C NMR (CDCl$_3$, 126 MHz): δ 171.7, 154.8, 131.1, 129.6, 128.7, 128.4, 127.1, 115.0, 80.9, 43.3, 37.4, 35.8, 25.5, 23.9, 23.6, 9.9; HRMS (ESI) m/z calcd for C$_{19}$H$_{23}$O$_3$ [M+H]$^+$ 299.1642, found 299.1644.

W. Synthesis of 3, 4-Diphenyl-1, 14-dioxadispiro [4.1.5$^7$.2$^5$] tetradec-3-en-2-one (23)

Following the General Procedure, to the mixture of (1-(3-phenylprop-2-yn-1-yl) cyclohexyl) methanol (0.1 g, 0.43 mmol) and ethyl phenylglyoxylate (0.078 g, 0.43 mmol) in anhydrous CH$_2$Cl$_2$ (5 mL) was added Bi(OTf)$_3$ (0.057 g, 0.086 mmol) under argon atmosphere at 27° C. and stirred the reaction mixture for 12 h. Purification of the crude product by crystallization (hexane:CH$_2$Cl$_2$ (8.2)) afforded 3, 4-diphenyl-1, 14-dioxadispiro [4.1.5$^7$.2$^5$] tetradec-3-en-2-one, (0.187 g, 73%) as a solid. TLC: R$_f$=0.5 (SiO$_2$, 20% EtOAc/hexanes); $^1$H NMR (CDCl$_3$, 400 MHz): δ 7.43-7.34 (m, 7H), 7.34-7.29 (m, 3H), 4.15 (d, J=8.4 Hz, 1H), 3.98 (d, J=8.4 Hz, 1H), 2.20 (d, J=13.7 Hz, 1H), 1.93 (d, J=13.7 Hz, 1H), 1.84-1.76 (m, 2H), 1.56-1.48 (m, 2H), 1.44-1.31 (m, 6H); $^{13}$C NMR (CDCl$_3$, 101 MHz): δ 169.8, 155.2, 131.0, 129.7, 129.5, 129.4, 128.9, 128.73, 128.71, 128.4, 114.4, 81.0, 43.4, 37.3, 35.8, 25.5, 23.9, 23.7; HRMS (ESI) m/z calcd for C$_{24}$H$_{25}$O$_3$ [M+H]$^+$ 361.1798, found 361.1798.

X. Synthesis of 3-(4-Methoxyphenyl)-4-phenyl-1, 14-dioxadispiro [4.1.5$^7$.2$^5$] tetradec-3-en-2-one (24)

Following the General Procedure, to the mixture of (1-(3-phenylprop-2-yn-1-yl) cyclohexyl) methanol (0.1 g, 0.43 mmol) and ethyl anisylglyoxylate (0.091 g, 0.43 mmol) in anhydrous CH$_2$Cl$_2$ (5 mL) was added Bi(OTf)$_3$ (0.057 g, 0.086 mmol) under argon atmosphere at 27° C. and stirred the reaction mixture for 12 h. Purification of the crude product by silica gel column chromatography (SiO$_2$, 5% EtOAc/hexanes) afforded 3-(4-methoxyphenyl)-4-phenyl-1, 14-dioxadispiro [4.1.5$^7$.2$^5$] tetradec-3-en-2-one (0.116 g, 68%) as a solid. TLC: R$_f$=0.45 (SiO$_2$, 20% EtOAc/hexanes);

¹H NMR (CDCl₃, 400 MHz): δ 7.46-7.33 (m, 7H), 6.82 (d, J=8.5 Hz, 2H), 4.13 (d, J=8.5 Hz, 1H), 3.95 (d, J=8.5 Hz, 1H), 3.81 (s, 3H), 2.17 (d, J=13.4 Hz, 1H), 1.90 (d, J=14.0 Hz, 1H), 1.82-1.74 (m, 2H), 1.54-1.47 (m, 2H), 1.43-1.25 (m, 6H); ¹³C NMR (CDCl₃, 101 MHz): δ 170.2, 160.0, 153.5, 131.4, 130.9, 129.5, 128.7, 128.7, 128.3, 121.7, 114.4, 113.8, 80.9, 55.2, 43.4, 37.3, 35.8, 29.7, 25.5, 23.9, 23.7; HRMS (ESI) m/z calcd for $C_{25}H_{27}O_4$ [M+H]⁺ 391.1904, found 391.1901.

Y. Synthesis of 4-Phenyl-3-(p-tolyl)-1, 14-dioxadispiro [4.1.5⁷.2⁵] tetradec-3-en-2-one (25)

Following the General Procedure, to the mixture of (1-(3-phenylprop-2-yn-1-yl) cyclohexyl) methanol (0.1 g, 0.43 mmol) and ethyl p-tolylglyoxylate (0.084 g, 0.43 mmol) in anhydrous CH₂Cl₂ (5 mL) was added Bi(OTf)₃ (0.057 g, 0.086 mmol) under argon atmosphere at 27° C. and stirred the reaction mixture for 12 h. Purification of the crude product by silica gel column chromatography (SiO₂, 3% EtOAc/hexanes) afforded 4-phenyl-3-(p-tolyl)-1, 14-dioxadispiro [4.1.5⁷.2⁵] tetradec-3-en-2-one (0.088 g, 66%) as a white solid. TLC: $R_f$=0.5 (SiO₂, 20% EtOAc/hexanes); ¹H NMR (CDCl₃, 500 MHz): δ 7.45-7.28 (m, 7H), 7.14-7.07 (m, 2H), 4.15 (d, J=8.5 Hz, 1H), 3.96 (d, J=8.5 Hz, 1H), 2.34 (s, 3H), 2.18 (d, J=13.4 Hz, 1H), 1.91 (d, J=14.0 Hz, 1H), 1.82-1.72 (m, 2H), 1.57-1.46 (m, 2H), 1.43-1.28 (m, 6H); ¹³C NMR (CDCl₃, 126 MHz): δ 170.0, 154.4, 138.9, 131.2, 129.6, 129.4, 129.1, 128.8, 128.7, 126.4, 114.4, 81.0, 46.5, 43.4, 37.3, 35.8, 25.5, 24.0, 23.7, 21.4; FIRMS (ESI) m/z calcd for $C_{25}H_{27}O_3$ [M+H]⁺ 375.1955, found 375.1956.

Z. Synthesis of 3-(4-Nitrophenyl)-4-phenyl-1, 14-dioxadispiro [4.1.5⁷.2⁵] tetradec-3-en-2-one (26)

Following the General Procedure, to the mixture of (1-(3-phenylprop-2-yn-1-yl) cyclohexyl) methanol (0.1 g, 0.43 mmol) and ethyl 2-(4-nitrophenyl)-2-oxoacetate (0.97 g, 0.43 mmol) in anhydrous CH₂Cl₂ (5 mL) was added Bi(OTf)₃ (0.057 g, 0.086 mmol) under argon atmosphere at 27° C. and stirred the reaction mixture for 12 h. Purification of the crude product by silica gel column chromatography (SiO₂, 3% EtOAc/hexanes) afforded 3-(4-nitrophenyl)-4-phenyl-1, 14-dioxadispiro [4.1.5⁷.2⁵] tetradec-3-en-2-one (0.125 g, 70%) as a yellow solid. TLC: $R_f$=0.65 (SiO₂, 20% EtOAc/hexanes); ¹H NMR (CDCl₃, 500 MHz): δ 8.16 (d, J=8.54 Hz, 2H), 7.61 (d, J=9.16 Hz, 2H), 7.51-7.35 (m, 5H), 4.17 (d, J=8.55 Hz, 1H), 3.98 (d, J=8.55 Hz, 1H), 2.22 (d, J=14.04 Hz, 1H), 1.93 (d, J=14.04 Hz, 1H), 1.84-1.74 (m, 2H), 1.56-1.48 (m, 2H), 1.44-1.25 (m, 6H); ¹³C NMR (CDCl₃, 126 MHz): δ 168.8, 158.4, 147.8, 130.6, 130.5, 129.2, 128.5, 123.5, 114.6, 81.3, 53.4, 43.6, 37.2, 35.8, 25.5, 23.9, 23.6; HRMS (ESI) m/z calcd for $C_{24}H_{24}O_5N$ [M+H]⁺ 406.1649, found 406.1640.

AA. Synthesis of 3-Methyl-4-phenyl-1, 13-dioxadispiro [4.1.4⁷.2⁵] tridec-3-en-2-one (27)

Following the General Procedure, to the mixture of (1-(3-phenylprop-2-yn-1-yl) cyclopentyl) methanol (0.05 gm, 0.23 mmol) and ethyl pyruvate (0.027 g, 0.23 mmol) in anhydrous CH₂Cl₂ (3 mL) was added Bi(OTf)₃ (0.03 g, 0.046 mmol) under argon atmosphere at 27° C. and stirred the reaction mixture for 12 h. Purification of the crude product by silica gel column chromatography (SiO₂, 3% EtOAc/hexane) afforded 3-methyl-4-phenyl-1, 13-dioxadispiro [4.1.4⁷.2⁵] tridec-3-en-2-one (0.036 g, 64%) as a solid. TLC: $R_f$=0.6 (SiO₂, 20% EtOAc/hexane); ¹H NMR (CDCl₃, 500 MHz,): δ 7.55-7.44 (m, 5H), 4.14 (d, J=8.0 Hz, 1H), 3.93 (d, J=8.0 Hz, 1H), 2.15-2.04 (m, 2H), 2.01 (s, 3H), 1.95-1.85 (m, 2H), 1.73-1.53 (m, 6H); ¹³C NMR (CDCl₃, 126 MHz): δ 171.7, 155.0, 131.1, 129.6, 128.7, 128.3, 127.1, 115.0, 81.5, 50.1, 47.0, 37.9, 37.7, 24.6, 24.3, 9.8; FIRMS (ESI) m/z calcd for $C_{18}H_{21}O_3$ [M+H] 285.1485, found 285.1482.

AB. Synthesis of 3-(4-Nitrophenyl)-4-phenyl-1, 13-dioxadispiro [4.1.4⁷.2⁵] tridec-3-en-2-one (28)

¹H NMR (CDCl₃, 400 MHz): δ 8.15 (m, J=8.5 Hz, 2H), 7.60 (d, J=8.5 Hz, 2H), 7.50-7.32 (m, 5H), 4.19 (d, J=7.9 Hz, 1H), 3.96 (d, J=7.9 Hz, 1H), 2.24 (d, J=13.4 Hz, 1H), 2.12 (d, J=14.0 Hz, 1H), 1.99-1.85 (m, 2H), 1.78-1.37 (m, 6H); ¹³C NMR (CDCl₃, 101 MHz): δ 168.7, 158.6, 147.7, 136.0, 130.54, 130.47, 130.2, 129.2, 128.5, 126.8, 123.5, 114.6, 81.9, 50.3, 47.0, 37.8, 37.5, 24.7, 24.3; HRMS (ESI) m/z calcd for $C_{23}H_{22}O_5N$ [M+H]⁺ 392.1492, found 392.1483.

AC. Synthesis of 3-Methyl-4-phenyl-1,6-dioxaspiro [4.4]non-3-en-2-one (29)

¹H NMR (CDCl₃, 400 MHz): δ 7.56-7.49 (m, 2H), 7.48-7.42 (m, 3H), 4.33 (dt, J=8.5, 4.3 Hz, 1H), 4.19-4.09 (m, 1H), 2.39-2.27 (m, 1H), 2.19-2.10 (m, 1H), 2.08-1.96 (m, 5H); ¹³C NMR (CDCl₃, 101 MHz): δ 171.5, 154.3, 131.1, 129.6, 128.7, 128.3, 127.3, 114.3, 70.4, 34.9, 24.4, 9.97; HRMS (ESI) m/z calcd for $C_{14}H_{15}O_3$ [M+H]⁺ 231.1016, found 231.1013.

AD. Synthesis of 3,4-Diphenyl-1,6-dioxaspiro[4.4] non-3-en-2-one (30)

¹H NMR (CDCl₃, 400 MHz): δ 7.46-7.23 (m, 10H), 4.37 (td, J=8.2, 3.7 Hz, 1H), 4.16 (m, 1H), 2.43-2.30 (m, 1H), 2.30-2.19 (m, 1H), 2.12-1.97 (m, 2H); ¹³C NMR (CDCl₃, 126 MHz): δ 169.7, 154.8, 131.0, 129.8, 129.5, 129.4, 129.1, 128.9, 128.8, 128.7, 128.4, 113.7, 70.7, 34.9, 24.5; HRMS (ESI) m/z calcd for $C_{19}H_{17}O_3$ [M+H]⁺ 293.1172, found 293.1168.

AE. Synthesis of 3-(4-Nitrophenyl)-4-phenyl-1, 6-dioxaspiro [4.4] non-3-en-2-one (31)

¹H NMR (CDCl₃, 500 MHz): δ 8.16 (d, J=8.8 Hz, 2H), 7.61 (d, J=8.8 Hz, 2H), 7.48-7.42 (m, 1H), 7.42-7.35 (m, 4H), 4.42 (td, J=8.4, 3.8 Hz, 1H), 4.21 (q, J=8.0 Hz, 1H), 2.45-2.35 (m, 1H), 2.35-2.27 (m, 1H), 2.15-2.01 (m, 2H); ¹³C NMR (CDCl₃, 126 MHz): δ 168.6, 157.9, 147.8, 136.0, 130.6, 130.5, 130.1, 129.2, 128.5, 127.1, 123.6, 113.9, 71.0, 34.9, 24.6; HRMS (ESI) m/z calcd for $C_{19}H_{16}O_5N$ [M+H]⁺ 338.1023, found 338.1018.

AF. Synthesis of 3-methyl-8, 8-diphenyl-1, 6-dioxaspiro [4.4] non-3-en-2-one (32)

¹H NMR (CDCl₃, 500 MHz) δ 7.36-7.28 (m, 5H), 7.28-7.22 (m, 3H), 7.21-7.18 (m, 2H), 6.35 (d, 1H), 4.86 (d, J=8.7 Hz, 1H), 4.49 (d, J=9.1 Hz, 1H), 3.27 (d, J=14.1 Hz, 1H), 2.95 (d, J=13.7 Hz, 1H), 1.86 (s, 3H); ¹³C NMR (CDCl₃, 126 MHz) δ 171.3, 145.6, 145.2, 143.6, 131.6, 128.7, 128.3, 127.1, 127.0, 126.8, 112.9, 77.9, 56.3, 47.5, 10.3; HRMS (ESI) m/z calcd for $C_{20}H_{19}O_3$ [M+H]⁺ 307.1326, found 307, 1329.

AG. Synthesis of 3, 8, 8-triphenyl-1, 6-dioxaspiro [4.4] non-3-en-2-one (33)

$^1$H NMR (CDCl$_3$, 400 MHz) δ 7.80-7.71 (m, 2H), 7.40-7.30 (m, 9H), 7.29-7.20 (m, 4H), 6.79 (s, 1H), 4.91 (d, J=9.1 Hz, 1H), 4.55 (d, J=9.1 Hz, 1H), 3.36 (d, J=14 Hz, 1H), 3.07 (d, J=14 Hz, 1H); $^{13}$C NMR (CDCl$_3$, 101 MHz) δ 169.1, 145.5, 143.5, 132.7, 129.8, 128.8, 128.7, 127.5, 127.1, 126.8, 112.1, 78.1, 56.4, 47.8; HRMS (ESI) m/z calcd for C$_{20}$H$_{19}$O$_3$ [M+H]$^+$ 307.1328, found 307.1329.

AH. Synthesis of 3-methyl-7-phenyl-1,6-dioxaspiro[4.4] non-3-en-2-one (34):

$^1$H NMR (CDCl$_3$, 500 MHz) δ 7.52-7.22 (m, 5H), 6.89 (s, 1H), 5.45 (t, J=5.72 Hz, 1H), 2.27-2.25 (m, 2H), 1.97 (s, 3H), 1.37-1.30 (m, 2H); $^{13}$C NMR (CDCl$_3$, 126 MHz) δ171.4, 144.3, 141.2, 133.3, 128.6, 128.5, 127.8, 125.4, 112.1, 82.4, 34.4, 32.5, 10.5; Diastereomer-2: TLC: R$_f$=0.28 (SiO$_2$, 20% EtOAc/hexanes); $^1$H NMR (CDCl$_3$, 400 MHz) δ 7.52-7.22 (m, 5H), 6.79 (s, 1H), 5.21 (t, J=4.88 Hz, 1H), 2.27-2.25 (m, 2H), 1.97 (s, 3H), 1.37-1.30 (m, 2H); $^{13}$C NMR (CDCl$_3$, 101 MHz) δ171.4, 144.5, 141.0, 133.5, 128.6, 128.4, 128.1, 126.3, 112.7, 85.0, 37.2, 34.1, 10.6; HRMS (ESI) m/z calcd for C$_{14}$H$_{15}$O$_3$[M+H]$^+$ 231.1016, found 231.1016.

AI. Synthesis of 4'-methyl-3a,4,5,6,7,7a-hexahydro-3H-1,5'H-spiro[benzofuran-2,2'-furan]-5'-one (35)

$^1$H NMR (CDCl$_3$, 400 MHz): δ 6.72 (s, 1H), 3.66-3.53 (m, 1H), 2.35 (dd, J=13.4, 7.9 Hz, 1H), 2.20-2.06 (m, 2H), 1.99-1.93 (m, 1H), 1.91 (s, 3H), 1.88 (d, J=11.6 Hz, 1H), 1.78 (d, J=7.3 Hz, 1H), 1.63-1.51 (m, 1H), 1.45-1.30 (m, 2H), 1.28-1.20 (m, 2H); $^{13}$C NMR (CDCl$_3$, 101 MHz): δ 171.9, 145.7, 131.2, 111.8, 84.7, 46.3, 39.8, 30.5, 28.5, 25.5, 24.0, 10.3; HRMS (ESI) m/z calcd for C$_{12}$H$_{17}$O$_3$ [M+H]$^+$ 209.1172, found 209.1173.

Minor diastereomer: $^1$H NMR (CDCl$_3$, 500 MHz): δ 6.72 (d, J=1.5 Hz, 1H), 3.39 (td, J=10.7, 3.8 Hz, 1H), 2.17-2.11 (m, 2H), 2.0 (d, J=14.1 Hz, 1H), 1.97-1.92 (m, 1H), 1.91 (d, J=1.5 Hz, 3H), 1.88-1.85 (m, 1H), 1.78-1.73 (m, 1H), 1.50 (qd, J=11.7, 3.8 Hz, 1H), 1.31-1.24 (m, 3H), 1.17 (td, J=12.2, 3.4 Hz, 1H); $^{13}$C NMR (CDCl$_3$, 126 MHz): δ 171.3, 145.9, 132.4, 111.4, 86.7, 43.7, 41.5, 31.3, 28.5, 25.5, 24.2, 10.4; HRMS (ESI) m/z calcd for C$_{12}$H$_{17}$O$_3$ [M+H]$^+$ 209.1172, found 209.1174.

AJ: Synthesis of 4-methyl-3a'-(prop-2-yn-1-yl)-3', 3a',4',8b'-tetrahydro-5H-spiro[furan-2,2'-indeno[1,2-b]furan]-5-one (36)

$^1$H NMR (CDCl$_3$, 500 MHz): δ 7.43-7.25 (m, 4H), 6.56 (s, 1H), 5.59 (s, 1H), 3.30 (d, J=16.5 Hz, 1H), 3.10 (d, J=17.1 Hz, 1H), 2.88 (AB q, J=17.0, 3.0 Hz, 2H), 2.50 (d, J=13.4 Hz, 1H), 2.21 (d, J=14.0 Hz, 1H), 1.99 (t, J=2.7 Hz, 1H), 1.93 (d, J=1.2 Hz, 3H); $^{13}$C NMR (CDCl$_3$, 126 MHz): δ 171.2, 144.5, 141.2, 140.8, 133.3, 129.4, 127.5, 125.7, 125.4, 113.2, 93.7, 81.4, 70.0, 52.6, 46.8, 43.0, 27.4, 10.5; HRMS (ESI) m/z calcd for C$_{18}$H$_{17}$O$_3$ [M+H]$^+$ 281.1172, found 281.1175.

Data for minor diastereomer (α-isomer): $^1$H NMR (CDCl$_3$, 400 MHz): δ 7.40 (d, J=7.3 Hz, 1H), 7.37-7.30 (m, 1H), 7.27-7.22 (m, 2H), 6.77 (s, 1H), 5.47 (s, 1H), 3.61 (d, J=16.5 Hz, 1H), 3.04 (d, J=16.5 Hz, 1H), 2.67-2.56 (m, 2H), 2.53-2.45 (m, 1H), 2.38 (d, J=13.4 Hz, 1H), 2.06 (s., 1H), 1.91 (s, 3H); $^{13}$C NMR (CDCl$_3$, 101 MHz): δ 171.4, 144.6, 142.7, 139.6, 133.3, 129.6, 127.4, 126.1, 125.3, 113.9, 94.4, 80.8, 70.6, 52.6, 46.5, 43.7, 28.4, 10.4; HRMS (ESI) m/z calcd for C$_{18}$H$_{17}$O$_3$ [M+H]$^+$ 281.1172, found 281.1175.

AK. Synthesis of 4-phenyl-3a'-(prop-2-yn-1-yl)-3', 3a',4',8b'-tetrahydro-5H-spiro[furan-2,2'-indeno[1,2-b]furan]-5-one (37)

$^1$H NMR (CDCl$_3$, 400 MHz): δ 7.79 (d, J=3.7 Hz, 2H), 7.50-7.00 (m, 13H), 5.63 (s, 1H), 3.80-2.80 (m, 9H), 2.61-2.47 (m, 5H), 2.40-1.90 (m, 4H); $^{13}$C NMR (CDCl$_3$, 101 MHz): δ 168.9, 143.1, 141.1, 140.8, 134.3, 129.9, 129.5, 128.8, 128.7, 127.6, 127.5, 127.4, 127.2, 125.8, 125.4, 125.3, 124.7, 112.4, 93.8, 81.4, 71.1, 70.2, 52.8, 50.6, 50.2, 48.8, 47.1, 43.7, 43.4, 42.9, 28.5, 27.4; HRMS (ESI) m/z calcd for C$_{23}$H$_{19}$O$_3$ [M+H]$^+$ 343.1329, found 343.1335.

AL. Synthesis of 4-methyl-3a'-(prop-2-yn-1-yl)-3', 4',5',9b'-tetrahydro-3'H,5H-spiro[furan-2,2'-naphtho[1,2-13]furan]-5-one (38)

$^1$H NMR (CDCl$_3$, 400 MHz): δ 7.38 (d, 7.3 Hz, 1H), 7.33-7.23 (m, 2H), 7.22-7.17 (m, 1H), 6.67 (s, 1H), 5.00 (s, 1H), 2.85-2.75 (m, 2H), 2.65-2.52 (m, 3H), 2.34 (d, J=14.0 Hz, 1H), 2.07-1.97 (m, 2H), 1.97-1.87 (m, 4H); $^{13}$C NMR (CDCl$_3$, 101 MHz): δ 171.5, 144.7, 137.2, 132.8, 132.3, 130.9, 128.7, 128.5, 126.7, 111.2, 83.9, 80.5, 70.8, 46.4, 43.9, 31.1, 26.6, 25.8, 10.4; HRMS (ESI) m/z calcd for C$_{19}$H$_{19}$O$_3$ [M+H]$^+$ 295.1319, found 295.1328.

Data for partially separable minor diastereomer: $^1$H NMR (CDCl$_3$, 500 MHz): δ 7.43-7.35 (m, 2H), 7.32-7.17 (m, 9H), 6.81 (d, J=1.1 Hz, 1H), 6.67 (d, J=1.5 Hz, 1H), 5.01 (s, 1H), 4.93 (s, 1H), 2.97-2.31 (m, 13H), 2.13-1.9 (m, 10H); $^{13}$C NMR (CDCl$_3$, 126 MHz): δ 171.5, 171.2, 145.7, 144.7, 137.2, 136.2, 132.9, 132.6, 132.3, 132.2, 130.9, 130.7, 128.7, 128.7, 128.5, 128.5, 126.7, 126.6, 111.9, 111.2, 83.9, 83.8, 80.5, 80.3, 71.5, 70.8, 46.6, 46.4, 43.9, 43.2, 31.2, 29.7, 28.3, 26.6, 25.8, 25.5, 10.4, 10.4; HRMS (ESI) m/z calcd for C$_{19}$H$_{19}$O$_3$ [M+H]$^+$ 295.13129, found 295.1319.

AM. Synthesis of 4-phenyl-3a'-(prop-2-yn-1-yl)-3', 4',5',9b'-tetrahydro-3'H,5H-spiro[furan-2,2'-naphtho[1,2-13]furan]-5-one (39)

$^1$H NMR (CDCl$_3$, 400 MHz): δ 7.89-7.79 (m, 2H), 7.48-7.10 (m, 12H), 5.08 (s, 1H), 3.5-2.2 (m, 12H), 2.16-1.75 (m, 5H); $^{13}$C NMR (CDCl$_3$, 101 MHz): δ 169.2, 144.2, 143.2, 137.2, 133.8, 132.2, 131.0, 130.8, 130.1, 129.8, 129.4, 128.8, 128.7, 128.6, 127.5, 126.8, 126.6, 126.5, 126.4, 110.4, 84.0, 83.9, 80.5, 71.4, 70.9, 51.1, 46.8, 46.7, 44.1, 42.8, 40.2, 31.2, 28.2, 26.6, 26.5, 25.8, 25.3; HRMS (ESI) m/z calcd for C$_{24}$H$_{21}$O$_3$ [M+H]$^+$ 357.1485, found 357.1473.

AN. Synthesis of (E)-3-Styryl-1,13-Dioxadispiro [4.1.4$^7$.2$^5$]Tridec-3-En-2-One (40)

$^1$H NMR (CDCl$_3$, 500 MHz) δ 7.71 (d, J=16.44 Hz, 1H), 7.51 (d, J=7.3 Hz, 2H), 7.39-7.30 (m, 5H), 6.90 (s, 1H), 6.81 (d, J=14.44 Hz, 1H), 4.70 (d, J=8.54 Hz, 1H), 3.91 (d, J=8.54 Hz, 1H) 2.27 (s, 2H), 1.93-1.84 (m, 2H), 1.52.-1.78 (m, 6H); $^{13}$C NMR (CDCl$_3$, 126 MHz) δ169.4, 143.0, 136.6, 136.2, 131.4, 29.1, 128.9, 128.8, 127.1, 116.1, 113.1, 81.2, 50.5, 47.8, 38.0, 37.2, 24.6, 24.4; HRMS (ESI) m/z calcd for C$_{19}$H$_{21}$O$_3$[M+H]$^+$ 297.1486, found 297.1485.

AO. Synthesis of 3-methyl-4, 8, 8-triphenyl-1, 6-dioxaspiro [4.4] non-3-en-2-one (41)

$^1$H NMR (CDCl$_3$, 400 MHz) δ 7.39-7.24 (m, 10H), 7.20-7.12 (m, 3H), 7.1-7.0 (m, 2H), 4.87 (d, J=9.1 Hz, 1H), 4.77 (d, J=9.7 Hz, 1H), 3.13 (d, J=14 Hz, 1H), 2.90 (d, J=14 Hz, 1H), 1.98 (s, 3H); $^{13}$C NMR (CDCl$_3$, 101 MHz) 171.3, 154.8, 146.1, 144.6, 130.4, 129.4, 128.5, 128.4, 128.4, 128.3, 127.7, 127.4, 126.7, 126.6, 126.4, 114.5, 79.3, 55.9, 48.2, 29.7, 9.8; HRMS (ESI) m/z calcd for C$_{26}$H$_{23}$O$_3$ [M+H]$^+$ 383.1642, found 383.1642.

AP. Synthesis of 4'-methyl-3'-phenyl-3a, 4, 5, 6, 7, 7a-hexahydro-3H, 5'H-spiro [benzofuran-2, 2'-furan]-5'-one (42)

$^1$H NMR (CDCl$_3$, 400 MHz) δ7.46-7.39 (s, 5H), 3.27-3.14 (td, J=4.27 10.38 Hz, 1H), 2.84 (dd, J=4.2, 3.6 Hz, 1H), 2.12-2.02 (m, 2H), 1.97 (s, 3H), 1.89-1.74 (m, 3H), 1.72-1.60 (m, 2H), 1.56-1.41 (m, 3H); $^{13}$C NMR (CDCl$_3$, 101 MHz) δ 171.5, 158.4, 136.0, 129.6, 129.0, 126.4, 123.2, 104.9, 44.5, 31.9, 31.7, 31.5, 31.2, 29.7, 29.4, 25.1, 24.5, 8.5; HRMS (ESI) m/z calcd for C$_{18}$H$_{21}$O$_3$ [M+H]$^+$ 285.1486, found 285.1485.

Data for minor diastereomer: $^1$H NMR (CDCl$_3$, 500 MHz) δ 7.56-7.44 (m, 5H), 3.75-3.64 (td, J=3.4 10.61H), 3.43-3.35 (td, J=3.43 10.68, 1H), 2.3-2.2 (m, 2H), 2.14-2.07 (m, 2H), 1.98-1.96 (s, 3H), 1.93-1.8 (m, 3H), 1.77-1.7 (m, 3H); HRMS (ESI) m/z calcd for C$_{18}$H$_{21}$O$_3$ [M+H]$^+$ 285.1487, found 285.1485.

Advantages of the Present Invention

1. Replacement of expensive noble metal catalysts with inexpensive and earth-abundant catalysts such as bismuth triflate in cascade annulation process.
2. The present catalytic approach possesses a dual activation capability, where it can activate triple bonds via oxy-functionalization and keto group of α-ketoesters.
3. Simple one step-operation, ambient reaction conditions, separation and easy-handling.
4. Easily accessible starting materials (alkynols and α-ketoesters) were used.
5. This one-pot cascade annulation will be most useful method to construct biologically potent natural/unnatural molecules and also in medicinal chemistry to carryout SAR studies.
6. Highly sterically demanding products, ambient reaction conditions, cost-effective catalytic system, good yields, operational simplicity, atom and step-economies.

We claim:

1. A γ-spiroketal-γ-lactones compound selected from a group consisting of 3-Methyl-1, 14-dioxadispiro [4.1.5$^7$.2$^5$] tetradec-3-en-2-one (1), 3-Phenyl-1, 14-dioxadispiro [4.4.5$^7$.2$^5$] tetradec-3-en-one (2), 3-(4-Methoxyphenyl)-1, 14-dioxadispiro [4.1.5$^7$.2$^5$] tetradec-3-en-2-one (3), 3-(p-Tolyl)-1, 14-dioxadispiro [4.1.5$^7$.2$^5$] tetradec-3-en-2-one (4), 3-Methyl-1, 13-dioxadispiro [4.1.4$^7$.2$^5$] tridec-3-en-2-one (5), 3-Phenyl-1, 13-dioxadispiro [4.1.4$^7$.2$^5$] tridec-3-en-one (6), 3-(4-Methoxyphenyl)-1, 13-dioxadispiro [4.1.4$^7$.2$^5$] tridec-3-en-2-one (7), 3-(p-Tolyl)-1, 13-dioxadispiro [4.1.4$^7$.2$^5$] tridec-3-en-2-one (8), 3-(4-Nitrophenyl)-1, 13-dioxadispiro [4.1.4$^7$.2$^5$] tridec-3-en-2 (9), 3-Methyl-1, 6-dioxaspiro [4.4] non-3-en-2-one (10), 3-Phenyl-1, 6-dioxaspiro [4, 4] non-3-en-2-one (11), 3-(4-Methoxyphenyl)-1, 6-dioxaspiro [4, 4] non-3-en-2-one (12), 3-(p-Tolyl)-1,6-dioxaspiro[4.4]non-3-en-2-one (13), 3, 4-Dimethyl-1, 14-dioxadispiro [4.1.5$^7$.2$^5$] tetradec-3-en-2-one (14), 4-Methyl-3-phenyl-1, 14-dioxadispiro [4.1.5$^7$.2$^5$] tetradec-3-en-2-one (15), 3-(4-Methoxyphenyl)-4-methyl-1, 14-dioxadispiro [4.1.5$^7$.2$^5$] tetradec-3-en-2-one (16), 4-Methyl-3-(p-tolyl)-1, 14-di oxadi spiro [4.1.5$^7$.2$^5$] tetradec-3-en-2-one (17), 4-Ethyl-3-methyl-1, 14-dioxadispiro [4.1.5$^7$.2$^5$] tetradec-3-en-2-one (18), 4-Ethyl-3-phenyl-1, 14-dioxadispiro [4.1.5$^7$.2$^5$] tetradec-3-en-2-one (19), 4-Ethyl-3-(4-methoxyphenyl)-1, 14-dioxadispiro [4.1.5$^7$.2$^5$] tetradec-3-en-2-one (20), 4-Ethyl-3-(p-tolyl)-1, 14-dioxadispiro [4.1.5$^7$.2$^5$] tetradec-3-en-2-one (21), 3-Methyl-4-phenyl-1, 14-dioxadispiro [4.1.5$^7$.2$^5$] tetradec-3-en-2-one (22), 3, 4-Diphenyl-1, 14-dioxadispiro [4.1.5$^7$.2$^5$] tetradec-3-en-2-one (23), 3-(4-Methoxyphenyl)-4-phenyl-1, 14-dioxadispiro [4.1.5$^7$.2$^5$] tetradec-3-en-2-one (24), 4-Phenyl-3-(p-tolyl)-1, 14-dioxadispiro [4.1.5$^7$.2$^5$] tetradec-3-en-2-one (25), 3-(4-Nitrophenyl)-4-phenyl-1, 14-dioxadispiro [4.1.5$^7$.2$^5$] tetradec-3-en-2-one (26), 3-Methyl-4-phenyl-1, 13-dioxadispiro [4.1.4$^7$.2$^5$] tridec-3-en-2-one (27), 3-(4-Nitrophenyl)-4-phenyl-1, 13-dioxadispiro [4.1.4$^7$.2$^5$] tridec-3-en-2-one (28), 3-Methyl-4-phenyl-1,6-dioxaspiro[4.4]non-3-en-2-one (29), 3-(4-Nitrophenyl)-4-phenyl-1, 6-dioxaspiro [4.4] non-3-en-2-one (31), 3-methyl-8, 8-diphenyl-1, 6-dioxaspiro [4.4] non-3-en-2-one (32), 3, 8, 8-triphenyl-1, 6-dioxaspiro [4.4] non-3-en-2-one (33), 3-methyl-7-phenyl-1,6-dioxaspiro [4.4]non-3-en-2-one (34), 4'-methyl-3a,4,5,6,7,7a-hexahydro-3H,5'H-spiro[benzofuran-2,2'-furan]-5'-one (35), 4-methyl-3a'-(prop-2-yn-1-yl)-3',3a',4',8b'-tetrahydro-5H-spiro[furan-2,2'-indeno[1,2-b]furan]-5-one (36), 4-phenyl-3 a'-(prop-2-yn-1-yl)-3',3 a',4', 8b'-tetrahydro-5H-spiro[furan-2,2'-indeno[1,2-b]furan]-5-one (37), 4-methyl-3a'-(prop-2-yn-1-yl)-3a',4',5',9b'-tetrahydro-3'H,5H-spiro[furan-2,2'-naphtho[1,2-b]furan]-5-one (38), 4-phenyl-3a'-(prop-2-yn-1-yl)-3a',4',5',9b'-tetrahydro-3'H,5H-spiro[furan-2,2'-naphtho[1,2-b]furan]-5-one (39), (E)-3-styryl-1,13-dioxadispiro[4.1.4$^7$.2$^5$]tridec-3-en-2-one (40), 3-methyl-4, 8, 8-triphenyl-1, 6-dioxaspiro [4.4] non-3-en-2-one (41), and 4'-methyl-3'-phenyl-3a, 4, 5, 6, 7, 7a-hexahydro-3H, 5'H-spiro [benzofuran-2, 2'-furan]-5'-one (42), or a stereoisomer, ester, hydrate, solvate or pharmaceutically acceptable salt thereof; and a pharmaceutically acceptable carrier, diluent or excipient.

2. A single step process for the preparation of a γ-spiroketal-γ-lactones compound selected from a group consisting of 3-Methyl-1, 14-dioxadispiro [4.1.5$^7$.2$^5$] tetradec-3-en-2-one (1), 3-Phenyl-1, 14-dioxadispiro [4.4.5$^7$.2$^5$] tetradec-3-en-one (2), 3-(4-Methoxyphenyl)-1, 14-dioxadispiro [4.1.5$^7$.2$^5$] tetradec-3-en-2-one (3), 3-(p-Tolyl)-1, 14-dioxadispiro [4.1.5$^7$.2$^5$] tetradec-3-en-2-one (4), 3-Methyl-1, 13-dioxadispiro [4.1.4$^7$.2$^5$] tridec-3-en-2-one (5), 3-Phenyl-1, 13-dioxadispiro [4.1.4$^7$.2$^5$] tridec-3-en-one (6), 3-(4-Methoxyphenyl)-1, 13-dioxadispiro [4.1.4$^7$.2$^5$] tridec-3-en-2-one (7), 3-(p-Tolyl)-1, 13-dioxadispiro [4.1.4$^7$.2$^5$] tridec-3-en-2-one (8), 3-(4-Nitrophenyl)-1, 13-dioxadispiro [4.1.4$^7$.2$^5$] tridec-3-en-2 (9), 3-Methyl-1, 6-dioxaspiro [4.4] non-3-en-2-one (10), 3-Phenyl-1, 6-dioxaspiro [4, 4] non-3-en-2-one (11), 3-(4-Methoxyphenyl)-1, 6-dioxaspiro [4, 4] non-3-en-2-one (12), 3-(p-Tolyl)-1,6-dioxaspiro[4.4]non-3-en-2-one (13), 3, 4-Dimethyl-1, 14-dioxadispiro [4.1.5$^7$.2$^5$] tetradec-3-en-2-one (14), 4-Methyl-3-phenyl-1, 14-dioxadispiro [4.1.5$^7$.2$^5$] tetradec-3-en-2-one (15), 3-(4-Methoxyphenyl)-4-methyl-1, 14-dioxadispiro [4.1.5$^7$.2$^5$] tetradec-3-en-2-one (16), 4-Methyl-3-(p-tolyl)-1, 14-di oxadi spiro [4.1.5$^7$.2$^5$] tetradec-3-en-2-one (17), 4-Ethyl-3-methyl-1, 14-dioxadispiro [4.1.5$^7$.2$^5$] tetradec-3-en-2-one (18), 4-Ethyl-3-phenyl-1, 14-dioxadispiro [4.1.5$^7$.2$^5$] tetradec-3-en-2-one (19), 4-Ethyl-3-(4-methoxyphenyl)-1, 14-dioxadispiro [4.1.5$^7$.2$^5$] tetradec-3-en-2-one (20), 4-Ethyl-3-(p-tolyl)-1, 14-dioxadispiro [4.1.5$^7$.2$^5$] tetradec-3-en-2-one (21), 3-Methyl-4-phenyl-1, 14-dioxadispiro [4.1.5$^7$.2$^5$] tetradec-3-en-2-one (22), 3, 4-Diphenyl-1, 14-dioxadispiro [4.1.5$^7$.2$^5$] tetradec-3-en-2-one (23), 3-(4-Methoxyphenyl)-4-phenyl-1, 14-dioxadispiro [4.1.5$^7$.2$^5$] tetradec-3-en-2-one (24), 4-Phenyl-3-(p-tolyl)-1, 14-dioxadispiro [4.1.5$^7$.2$^5$] tetradec-3-en-2-one (25), 3-(4-Nitrophenyl)-4-phenyl-1, 14-dioxadispiro [4.1.5$^7$.2$^5$] tetradec-3-en-2-one (26), 3-Methyl-4-phenyl-1, 13-dioxadispiro [4.1.4$^7$.2$^5$] tridec-3-en-2-one (27), 3-(4-Nitrophenyl)-4-phenyl-1, 13-dioxadispiro [4.1.4$^7$.2$^5$] tridec-3-en-2-one (28), 3-Methyl-4-phenyl-1,6-dioxaspiro[4.4]non-3-en-2-one (29), 3-(4-Nitrophenyl)-4-phenyl-1, 6-dioxaspiro [4.4] non-3-en-2-one (31), 3-methyl-8, 8-diphenyl-1, 6-dioxaspiro [4.4] non-3-en-2-one (32), 3, 8, 8-triphenyl-1, 6-dioxaspiro [4.4] non-3-en-2-one (33), 3-methyl-7-phenyl-1,6-dioxaspiro[4 0.4]non-3-en-2-one (34), 4'-methyl-3 a,4,5, 6,7, 7a-hexahydro-3H, 5'H-spiro[benzofuran-2,2'-furan]-5'-one (35), 4-methyl-3 a'-(prop-2-yn-1-yl)-3 ',3 a',4', 8b'-tetrahydro-5H-spiro[furan-2,2'-indeno[1,2-b]furan]-5-one (36), 4-phenyl-3 a'-(prop-2-yn-1-yl)-3 ',3 a',4',8b'-tetrahydro-5H-spiro[furan-2,2'-indeno[1,2-b]furan]-5-one (37), 4-methyl-3 a'-(prop-2-yn-1-yl)-3 a',4', 5',9b'-tetrahydro-3 'H, 5H-spiro[furan-2,2'-naphtho [1,2-b]furan]-5-one (38), 4-phenyl-3 a'-(prop-2-yn-1-y1)-3 a',4',5',9b'-tetrahydro-3'H,5H-spiro[furan-2,2'-naphtho[1,2-b]furan]-5-one (39), (E)-3-styryl-1,13-dioxadispiro[4.1.4$^7$.2$^5$]tridec-3-en-2-one (40), 3-methyl-4, 8, 8-triphenyl-1, 6-dioxaspiro [4.4] non-3-en-2-one (41), and 4'-methyl-3'-phenyl-3a, 4, 5, 6, 7, 7a-hexahydro-3H, 5'H-spiro [benzofuran-2, 2'-furan]-5'-one (42), or a stereoisomer, ester, hydrate, solvate or pharmaceutically acceptable salt thereof; and a pharmaceutically acceptable carrier, diluent or excipient, the process comprising:

adding a catalyst in a solution of alkynol and an α-ketoester in a solvent at a temperature ranging from 25° C. to 30° C. followed by stirring the reaction mixture at the temperature ranging from 25° C. to 30° C. for a time period ranging from 12 to 48 hours;

wherein the catalyst is selected from a group consisting of bismuth triflate, Copper (II) triflate, Scandium(III) triflate, Ferric triflate, mercuric triflate, Ytterbium triflate, Iron(III) chloride, Silver triflate, p-Toluenesulfonic acid, and Trifluoromethanesulfonic acid;

wherein the alkynol is selected from a group consisting of (1-(Prop-2-yn-1-yl) cyclohexyl) methanol; (1-(But-2-yn-1-yl) cyclohexyl) methanol; (1-(Pent-2-yn-1-yl) cyclohexyl) methanol; (1-(3-Phenylprop-2-yn-1-yl) cyclohexyl); (1-(Prop-2-yn-1-yl) cyclopentyl) methanol; (1-(3-Phenylprop-2-yn-1-yl) cyclopentyl) methanol; 5-Phenylpent-4-yn-1-ol; 2, 2-diphenylpent-4-yn-1-ol; 1-phenylpent-4-yn-1-ol; 2-(prop-2-yn-1-yl) cyclohexan-1-ol; 2,2-di(prop-2-yn-1-yl)-2,3-dihydro-1H-inden-1-ol; 2,2-di(prop-2-yn-1-yl)-1,2,3,4-tetrahydronaphthalen-1-ol; 2,2,5-triphenylpent-4-yn-1-ol;

and 2-(3-phenylprop-2-yn-1-yl) cyclohexan-1-ol;

wherein the α-ketoester is selected from a group consisting of ethyl 2-(4-nitrophenyl)-2-oxoacetate, ethyl pyruvate, ethyl phenylglyoxylate, ethyl anisylglyoxylate, ethyl p-tolylglyoxylate, and ethyl (E)-2-oxo-4-phenylbut-3-enoate; and wherein the solvent is selected from the group consisting of dicholoromethane, toluene, acetonitrile, tetrahydrofuran, and nitromethane.

3. The process as claimed in 2, wherein the yield of the process is ranging from 40-80%.

4. A pharmaceutical composition comprising a γ-spiroketal-γ-lactones compound selected from the group consisting of 3-Methyl-1, 14-dioxadispiro [4.1.5$^7$.2$^5$] tetradec-3-en-2-one (1), 3-Phenyl-1, 14-dioxadispiro [4.4.5$^7$.2$^5$] tetradec-3-en-one (2), 3-(4-Methoxyphenyl)-1, 14-dioxadispiro [4.1.5$^7$.2$^5$] tetradec-3-en-2-one (3), 3-(p-Tolyl)-1, 14-dioxadispiro [4.1.5$^7$.2$^5$] tetradec-3-en-2-one (4), 3-Methyl-1, 13-dioxadispiro [4.1.4$^7$.2$^5$] tridec-3-en-2-one (5), 3-Phenyl-1, 13-dioxadispiro [4.1.4$^7$.2$^5$] tridec-3-en-one (6), 3-(4-Methoxyphenyl)-1, 13-dioxadispiro [4.1.4$^7$.2$^5$] tridec-3-en-2-one (7), 3-(p-Tolyl)-1, 13-dioxadispiro [4.1.4$^7$.2$^5$] tridec-3-en-2-one (8), 3-(4-Nitrophenyl)-1, 13-dioxadispiro [4.1.4$^7$.2$^5$] tridec-3-en-2 (9), 3-Methyl-1, 6-dioxaspiro [4.4] non-3-en-2-one (10), 3-Phenyl-1, 6-dioxaspiro [4, 4] non-3-en-2-one (11), 3-(4-Methoxyphenyl)-1, 6-dioxaspiro [4, 4] non-3-en-2-one (12), 3-(p-Tolyl)-1,6-dioxaspiro[4.4]non-3-en-2-one (13), 3, 4-Dimethyl-1, 14-dioxadispiro [4.1.5$^7$.2$^5$] tetradec-3-en-2-one (14), 4-Methyl-3-phenyl-1, 14-dioxadispiro [4.1.5$^7$.2$^5$] tetradec-3-en-2-one (15), 3-(4-Methoxyphenyl)-4-methyl-1, 14-dioxadispiro [4.1.5$^7$.2$^5$] tetradec-3-en-2-one (16), 4-Methyl-3-(p-tolyl)-1, 14-dioxadispiro [4.1.5$^7$.2$^5$] tetradec-3-en-2-one (17), 4-Ethyl-3-methyl-1, 14-dioxadispiro [4.1.5$^7$.2$^5$] tetradec-3-en-2-one (18), 4-Ethyl-3-phenyl-1, 14-dioxadispiro [4.1.5$^7$.2$^5$] tetradec-3-en-2-one (19), 4-Ethyl-3-(4-methoxyphenyl)-1, 14-dioxadispiro [4.1.5$^7$.2$^5$] tetradec-3-en-2-one (20), 4-Ethyl-3-(p-tolyl)-1, 14-dioxadispiro [4.1.5$^7$.2$^5$] tetradec-3-en-2-one (21), 3-Methyl-4-phenyl-1, 14-dioxadispiro [4.1.5$^7$.2$^5$] tetradec-3-en-2-one (22), 3, 4-Diphenyl-1, 14-dioxadispiro [4.1.5$^7$.2$^5$] tetradec-3-en-2-one (23), 3-(4-Methoxyphenyl)-4-phenyl-1, 14-dioxadispiro [4.1.5$^7$.2$^5$] tetradec-3-en-2-one (24), 4-Phenyl-3-(p-tolyl)-1, 14-dioxadispiro [4.1.5$^7$.2$^5$] tetradec-3-en-2-one (25), 3-(4-Nitrophenyl)-4-phenyl-1, 14-dioxadispiro [4.1.5$^7$.2$^5$] tetradec-3-en-2-one (26), 3-Methyl-4-phenyl-1, 13-dioxadispiro [4.1.4$^7$.2$^5$] tridec-3-en-2-one (27), 3-(4-Nitrophenyl)-4-phenyl-1, 13-dioxadispiro [4.1.4$^7$.2$^5$] tridec-3-en-2-one (28), 3-Methyl-4-phenyl-1,6-dioxaspiro[4.4]non-3-en-2-one (29), 3-(4-Nitrophenyl)-4-phenyl-1, 6-dioxaspiro [4.4] non-3-en-2-one (31), 3-methyl-8, 8-diphenyl-1, 6-dioxaspiro [4.4] non-3-en-2-one (32), 3, 8, 8-triphenyl-1, 6-dioxaspiro [4.4] non-3-en-2-one (33), 3-methyl-7-phenyl-1,6-dioxaspiro [4.4]non-3-en-2-one (34), 4'-methyl-3 a, 4,5, 6,7, 7a-hexahydro-3H, 5'H-spiro[benzofuran-2,2'-furan]-5'-one (35), 4-methyl-3 a'-(prop-2-yn-1-yl)-3 ',3 a',4', 8b'-tetrahydro-5H-spiro[furan-2,2'-indeno[1,2-b]furan]-5-one (36), 4-phenyl-3 a'-(prop-2-yn-1-yl)-3 ',3 a',4',8b'-tetrahydro-5H-spiro [furan-2,2'-indeno[1,2-b]furan]-5-one (37), 4-methyl-3 a'-(prop-2-yn-1-yl)-3 a',4', 5',9b'-tetrahydro-3 'H, 5H-spiro [furan-2, 2'-naphtho [1, 2-b]furan]-5-one (38), 4-phenyl-3 a'-(prop-2-yn-1-y1)-3 a',4', 5',9b'-tetrahydro-3 'H, 5H-spiro [furan-2,2'-naphtho[1,2-b]furan]-5-one (39), (E)-3-styryl-1, 13-dioxadispiro[4.1.4$^7$.2$^5$]tridec-3-en-2-one (40), 3-methyl-4, 8, 8-triphenyl-1, 6-dioxaspiro [4.4] non-3-en-2-one (41), and 4'-methyl-3'-phenyl-3a, 4, 5, 6, 7, 7a-hexahydro-3H, 5'H-spiro [benzofuran-2, 2'-furan]-5'-one (42), or a stereoisomer, ester, hydrate, solvate or pharmaceutically acceptable salt thereof; and a pharmaceutically acceptable carrier, diluent or excipient.

* * * * *